US008183268B2

(12) United States Patent
Loso et al.

(10) Patent No.: US 8,183,268 B2
(45) Date of Patent: *May 22, 2012

(54) HETEROARYL (SUBSTITUTED)ALKYL N-SUBSTITUTED SULFOXIMINES AS INSECTICIDES

(75) Inventors: Michael R. Loso, Carmel, IN (US); Benjamin M. Nugent, Brownsburg, IN (US); Yuanming Zhu, Carmel, IN (US); Richard B. Rogers, Mobile, AL (US); Jim X. Huang, Carmel, IN (US); James M. Renga, Indianapolis, IN (US); Gregory T. Whiteker, Carmel, IN (US); Nneka T. Breaux, Indianapolis, IN (US); John F. Daeuble, Carmel, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 211 days.

This patent is subject to a terminal disclaimer.

(21) Appl. No.: 12/721,752

(22) Filed: Mar. 11, 2010

(65) Prior Publication Data
US 2010/0168172 A1  Jul. 1, 2010

(51) Int. Cl.
*A01N 43/76* (2006.01)
(52) U.S. Cl. ........................................ 514/357
(58) Field of Classification Search .............. 514/357
See application file for complete search history.

(56) References Cited

U.S. PATENT DOCUMENTS

| | | | |
|---|---|---|---|
| 3,711,486 A | 1/1973 | Torba et al. | |
| 3,787,420 A | 1/1974 | Torba et al. | |
| 3,852,279 A | 12/1974 | Krapcho et al. | |
| 4,577,028 A | 3/1986 | Martin et al. | |
| 4,692,184 A | 9/1987 | Lee | |
| 4,747,871 A | 5/1988 | Ruminski et al. | |
| 4,833,158 A | 5/1989 | Twydell et al. | |
| 4,948,896 A | 8/1990 | Nagao | |
| 4,973,695 A | 11/1990 | Yamashita et al. | |
| 5,053,516 A | 10/1991 | Hartmann et al. | |
| 5,099,023 A | 3/1992 | Miller et al. | |
| 5,099,024 A | 3/1992 | Pulwer et al. | |
| 5,118,809 A | 6/1992 | Cevasco et al. | |
| 5,124,458 A | 6/1992 | Cevasco et al. | |
| 5,169,432 A | 12/1992 | Auinbauh et al. | |
| 5,225,560 A | 7/1993 | Cevasco et al. | |
| 5,227,491 A | 7/1993 | Doehner, Jr. | |
| 5,229,519 A | 7/1993 | Zhang et al. | |
| 6,060,502 A | 5/2000 | Louder et al. | |
| 7,511,149 B2 | 3/2009 | Arndt et al. | |
| 7,541,469 B2 | 6/2009 | Renga et al. | |
| 7,604,815 B2 | 10/2009 | Loso et al. | |
| 7,678,920 B2 | 3/2010 | Zhu et al. | |
| 2003/0078430 A1 | 4/2003 | Satake et al. | |
| 2004/0158067 A1 | 8/2004 | Hutchison et al. | |
| 2006/0199964 A1 | 9/2006 | Jackson et al. | |
| 2007/0203191 A1 | 8/2007 | Loso et al. | |
| 2007/0249837 A1 | 10/2007 | Gebhardt et al. | |
| 2007/0299264 A1* | 12/2007 | Huang et al. ............ 546/281.4 |
| 2008/0108665 A1 | 5/2008 | Huang et al. | |
| 2008/0108666 A1 | 5/2008 | Loso et al. | |
| 2008/0108667 A1 | 5/2008 | Zhu et al. | |
| 2008/0132705 A1 | 6/2008 | Heller et al. | |
| 2008/0194830 A1 | 8/2008 | Meyer et al. | |
| 2008/0280915 A1 | 11/2008 | Loso et al. | |
| 2010/0144794 A1* | 6/2010 | Loso et al. ................ 514/336 |
| 2010/0144803 A1* | 6/2010 | Loso et al. ................ 514/357 |
| 2010/0152245 A1* | 6/2010 | Loso et al. ................ 514/336 |
| 2010/0179099 A1* | 7/2010 | Loso et al. ................. 514/28 |
| 2010/0179197 A1* | 7/2010 | Zhu et al. ................. 514/351 |

FOREIGN PATENT DOCUMENTS

| | | |
|---|---|---|
| DE | 19523658 | 6/1995 |
| WO | WO98/02492 | 1/1998 |
| WO | WO01/07430 | 2/2001 |

OTHER PUBLICATIONS

Kagabu, Shinzo and Medej, Somporn; "Stability Comparison of Imidacloprid and Related Compounds under Simulated Sunlight, Hydrolysis Conditions, and to Oxygen;" Biosci. Biotech. Biochem., 59 (6), 980-985, (1995).
Kagabu, Shinzo; Murata, Natsue; Hibino, Rika; Hanzawa, Madoka and Nishimura, Keiichiro; "Insecticidal and Neuroblocking Activities of Thiamethoxam-Type Compounds in the American Cockroach (Periplaneta americana L.);" J. Pesticide Sci. 30(2), 111-115 (2005).
Sparks, Thomas C.; Crouse, Gary D. and Durst, Gregory; "Natural products as insecticides: the biology, biochemistry and quantitative structure-activity relationships of spinosyns and spinosoids;" Pest Management Science, 57:896-905 (2001).
Wakita, Takeo; Kinoshita, Katsutoshi; Kodaka, Kenji; Yasui, Naoko; Naoi, Atsuko and Banba, Sinichi; "Synthesis and Structure-Activity Relationships of Dinotefuran Derivatives: Modification in the Tetrahydro-3-furylmethyl Part;" J. Pesticide Sci. 29 (4), 356-363 (2004).
Kollmeyer, Willy D.; Flattum, Roger F.; Foster, James P.; Powell, James E.; Schroeder, Mark E. and Soloway, S. Barney; "Discovery of the Nitromethylene Heterocycle Insecticides;" Nicotinoid Insecticides and the Nicotinic Acetylcholine Receptor [Eds.: Yamamoto, I. and Casida, J.E.]; 1999, pp. 71-89, Springer-Verlag, Tokyo.
Shiga, Yasushi; Okada, Itaru and Fukuchi, Toshiki; "Synthesis and Acaricidal Activity of N-(1,3,4-Thiadiazol-2-yl)cyclopropanecarboxamides;" J. Pesticide Sci. 28, 61-63 (2003).
Singer, Alvin; McElvain, S.M. 2,6-Dimethylpyridine. Organic Syntheses, 1934, 14, 30.
Haibo Yu, Zhenfang Qin, Hong Dai, Xin Zhang, Xue Qin, Tingting Wang and Jianxin Fang, Synthesis and Insecticidal Activity of N-Substituted (1,3-Thiazole)alkyl Sulfoximine Derivatives, J. Agric. Food Chem. 2008, 56, 11356-11360.
Haibo Yu, Zhenfang Qin, Hong Dai, Xin Zhang, Xue Qin, Tingting Wang, and Jianxin Fang, Synthesis and insecticidal activity of N-cyano 2-(substituted amino) ethyl methyl sulfoximine derivatives, General Papers, ARKIVOC 2008 (xvi) 99-109.
Kawanshi, Hiroyuki; Morimoto, Hiroshi; Nakano, Takao; Watanabe, Tatsuya; Oda, Kuniyuki; and Tsujihara, Kenji; "Steroselective Synthesis of Antifungal Sulfoximines, Novel Trizaoles II;" Heterocycles, vol. 49, 1998, pp. 181-189.

(Continued)

Primary Examiner — Janet Andres
Assistant Examiner — John Mabry
(74) Attorney, Agent, or Firm — Carl D. Corvin

(57) ABSTRACT

N-Substituted heteroaryl (substituted)alkyl sulfoximines are effective at controlling insects.

8 Claims, No Drawings

OTHER PUBLICATIONS

Reichert, Anja; Frohlich, Roland; Ferguson, Roderick; Kraft, Arno; "Binding Interactions Between 3-aryl-1,2,4-oxadiazol-5-ones and a trisimidazoline base;" J. Chem. Soc., Perkin Trans. 1, 2001, pp. 1321-1328.

Garcia Mancheno, Olga; Bistri, Olivia; and Bolm, Carsten; "Iodinane- and Metal-Free Synthesis of N-Cyano Sulfilimines: Novel and Easy Access of NH-Sulfoximines;" Organic Letters, 2007, vol. 9, No. 19, pp. 3809-3811.

Kiriyama K et al: Insecticidal and neuroblocking activities of acetamiprid and related compounds Journal of Pesticide Sciences, Pesticide Science Society, Tokyo, JP, vol. 28, No. 1, 2003, pp. 80-17.

F Zaragoza Dorwald Side Reactions in Organic Synthesis 2005, Wiley-VCH.

ortho Lithiation of S-ter-butyl-S-phenylsulfoximines (Tetrahedron), Stephane Gaillard, Mar. 29, 2005.

Yoshide et al: "The Cycloaddition Reaction of N-Imidoyl Sulfoximides with Diphenylcyclopropenone to Yield Pyrimidinone or Pyrrolinone Derivatives" The Chemical Society of Japan, Sep. 29, 1982.

Veale et al: "New Method in Preparation of Acyl- and Sulfonysulfoximines Ruthenium Tetroxide Oxidation of Sulfilmines" Tetrahedron Letters, No. 6, pp. 503-506, 1978.

Whittle et al: "Rearrangement Process in the Mass Spectra of N-Substituted Sulphoximines" Organic Mass Spectrometry, 1974, vol. 9, pp. 422-434.

Huang et al: "Oxidation of N-Acyl-, and N-Arylsulfilimines to Sulfoximines by m-Chloroperoxybenzoate Anion" J Org Chem, vol. 44 No. 14, 1979.

Garapon et al: "No 500—Reactions d'elminiations sur les o-chlorobenzoates d/anilide-oximes: formation des aryliminonitrenes sous l'action des bases azotees" Instiut Francois de Pelrole, B P 85, 38041, 1975.

Williams, Trevor et al., Biocontrol Science and Technology, "Is the Naturally Derived Insecticide Spinosad Compatible with Insect Natural Enemies", Aug. 2003, vol. 13, No. 15, pp. 459-475.

* cited by examiner

HETEROARYL (SUBSTITUTED)ALKYL N-SUBSTITUTED SULFOXIMINES AS INSECTICIDES

This application claims the benefit of U.S. Provisional Application Ser. No. 60/857,708 filed on 8 Nov. 2006. This application also claims the benefit of U.S. application Ser. No. 11/704,797 filed on 9 Feb. 2007.

BACKGROUND OF THE INVENTION

The present invention concerns novel heteroaryl (substituted)alkyl N-substituted sulfoximines as insecticides and their use in controlling insects, particularly aphids and other sucking insects, as well as certain other invertebrates. This invention also includes new synthetic procedures for preparing the compounds, pesticide compositions containing the compounds, and methods of controlling insects using the compounds.

There is an acute need for new insecticides. Insects are developing resistance to the insecticides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides. Therefore a need exists for new insecticides, and particularly for compounds that have new or atypical modes of action.

U.S. Patent Application Publication 2005/0228027 A1 describes certain pyridyl-, thiazolyl-, and isoxazolyl(substituted)alkyl N-substituted sulfoximine compounds and their use in controlling insects. However, only methyl, ethyl, and halogen substituents are disclosed in the hydrocarbon backbone of these compounds. It has now been discovered that a wider array of substitution produces similarly active compounds with uniquely advantageous properties or attributes including, but not limited to, properties better suited for formulations typically used for foliar applications to control insects.

SUMMARY OF THE INVENTION

This invention concerns compounds useful for the control of insects, especially useful for the control of aphids and other sucking insects. More specifically, the invention concerns compounds of formula (I)

$$\text{Het}-[CH_2]_n-[\overset{R^2}{\underset{}{C}}\overset{R^3}{\underset{}{}}]-[\overset{R^4}{\underset{}{C}}\overset{R^5}{\underset{}{}}]_m-\underset{O}{\overset{}{S}}(=N-X)-R^1 \quad (I)$$

wherein
Het represents

[four heterocyclic structures: thiazole (Y at 2-position, attachment at 4), thiazole (Y at 2-position, attachment at 4 with N/S reversed), isoxazole (Y at 3-position, attachment at 5), and pyridine (Y at 6-position, attachment at 3)]

Y represents halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, CN, $NO_2$, or $SO_pR^6$ and p is an integer from 0-2;

X represents $NO_2$, CN, $COOR^7$
n and m independently represent integers from 0-1;
$R^1$ represents $C_1$-$C_4$ alkyl, $C_1$-$C_4$ haloalkyl or, alternatively, is taken together with either $R^3$ or $R^5$ to form a saturated 4-, 5-, or 6-membered ring;
$R^2$ represents H, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkoxy substituted $C_1$-$C_4$ alkyl, halo, CN, $SO_pR^6$, $COOR^7$, $COR^S$, $CONR^7R^8$, aryl, heteroaryl, arylalkyl, heteroarylalkyl, or alternatively, $R^2$ taken together with the ortho-carbon of Het form a saturated 5- or 6-membered ring optionally containing an O or N atom, with the proviso that when $R^2$ represents H then m=1 and either $R^3$ or $R^4$ represents something other than H;
$R^3$ represents H, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkoxy substituted $C_1$-$C_4$ alkyl, halo, CN, $SO_pR^6$, $COOR^7$, $CONR^7R^8$, aryl, heteroaryl, arylalkyl, heteroarylalkyl, or alternatively, $R^3$ taken together with $R^4$ form a saturated 3-, 4-, 5- or 6-membered ring optionally containing an O or N atom, or $R^3$ taken together with $R^1$ form a saturated 4-, 5-, or 6-membered ring, or $R^2$ and $R^3$ taken together form an olefin (=$CH_2$), a ketone (=O), or an imine (=$NR^7$);
$R^4$ represents H, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, CN, $SO_pR^6$, $COOR^7$, $CONR^7R^8$, aryl, heteroaryl, arylalkyl, heteroarylalkyl, or alternatively, $R^4$ taken together with $R^3$ form a saturated 3-, 4-, 5- or 6-membered ring optionally containing an O or N atom;
$R^5$ represents H, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, CN, $SO_pR^6$, $COOR^7$, $CONR^7R^8$, aryl, heteroaryl, arylalkyl, heteroarylalkyl, or alternatively, $R^5$ taken together with $R^1$ form a saturated 4-, 5- or 6-membered ring;
$R^6$ represents $C_1$-$C_4$ alkyl or $C_1$-$C_4$ haloalkyl;
$R^7$ represents $C_1$-$C_4$ alkyl; $C_1$-$C_4$ haloalkyl, $C_3$-$C_6$ alkenyl, $C_3$-$C_6$ alkynyl, $C_3$-$C_6$ haloalkenyl, aryl, heteroaryl, arylalkyl, or heteroarylalkyl; and
$R^8$ represents H, $C_1$-$C_4$ alkyl; $C_1$-$C_4$ haloalkyl, $C_3$-$C_6$ alkenyl, $C_3$-$C_6$ alkynyl, $C_3$-$C_6$ haloalkenyl, aryl, heteroaryl, arylalkyl, or heteroarylalkyl;
with the proviso that when Het represents 6-halopyridin-3-yl, 6-($C_1$-$C_4$)alkyl-pyridin-3-yl, 6-($C_1$-$C_4$)alkoxypyridin-3-yl, 6-($C_1$-$C_4$)haloalkylpyridin-3-yl, 2-chlorothiazol-4-yl, 2-chlorothiazol-5-yl, or 3-chloroisoxazol-5-yl, then $R^2$, $R^3$, $R^4$ and $R^5$ do not represent hydrogen, methyl, ethyl or halo.
Preferred compounds of formula (I) include the following classes:

(1) Compounds of formula (I) wherein Het represents

[pyridine structure with Y at 6-position, attachment at 3]

(2) Compounds of formula (I) wherein Y is halo, preferably Cl, or $C_1$-$C_4$ haloalkyl, preferably trihalomethyl, most preferably $CF_3$;
(3) Compounds of formula (I) wherein X is $NO_2$ or CN, most preferably CN;
(4) Compounds of formula (I) wherein m and n represent 0;
(5) Compounds of formula (I) wherein $R^1$ represents $CH_3$ or $CH_2CH_3$, most preferably $CH_3$;

(6) Compounds of formula (I) wherein $R^2$ represents $C_1$-$C_4$ alkyl, $C_1$-$C_4$ haloalkyl, $C_2$-$C_4$ haloalkenyl, $C_2$-$C_4$ alkynyl, $C_1$-$C_4$ alkoxy substituted $C_1$-$C_4$ alkyl, arylalkyl or heteroarylalkyl and $R^3$ represents hydrogen.

(7) Compounds of formula (I) wherein $R^3$ taken together with $R^1$ forms a 5-membered ring, e.g.,

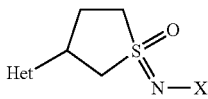

(8) Compounds of formula (I) wherein $R^3$ taken together with $R^4$ forms a 5-membered ring, e.g.,

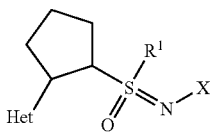

It will be appreciated by those skilled in the art that the most preferred compounds are generally those which are comprised of combinations of the above preferred classes.

The invention also provides new processes for preparing compounds of formula (I) as well as new compositions and methods of use, which will be described in detail hereinafter.

DETAILED DESCRIPTION OF THE INVENTION

Throughout this document, all temperatures are given in degrees Celsius, and all percentages are weight percentages unless otherwise stated.

Unless specifically limited otherwise, the terms "alkyl", "alkenyl" and "alkynyl", as well as derivative terms such as "alkoxy", "acyl", "alkylthio", "arylalkyl", "heteroarylalkyl" and "alkylsulfonyl", as used herein, include within their scope straight chain, branched chain and cyclic moieties. Thus, typical alkyl groups are methyl, ethyl, 1-methylethyl, propyl, 1,1-dimethylethyl, and cyclo-propyl. Unless specifically stated otherwise, each may be unsubstituted or substituted with one or more substituents selected from but not limited to halogen, hydroxy, alkoxy, alkylthio, $C_1$-$C_6$ acyl, formyl, cyano, aryloxy or aryl, provided that the substituents are sterically compatible and the rules of chemical bonding and strain energy are satisfied. The term "haloalkyl" and "haloalkenyl" includes alkyl and alkenyl groups substituted with from one to the maximum possible number of halogen atoms, all combinations of halogens included. The term "halogen" or "halo" includes fluorine, chlorine, bromine and iodine, with fluorine being preferred. The terms "alkenyl" and "alkynyl" are intended to include one or more unsaturated bonds.

The term "aryl" refers to a phenyl, indanyl or naphthyl group. The term "heteroaryl" refers to a 5- or 6-membered aromatic ring containing one or more heteroatoms, viz., N, O or S; these heteroaromatic rings may be fused to other aromatic systems. Such heteroaromatic rings include, but are not limited to furanyl, thienyl, pyrrolyl, pyrazolyl, imidazolyl, triazolyl, isoxazolyl, oxazolyl, thiazolyl, isothiazolyl, pyridyl, pyridazyl, pyrimidyl, pyrazinyl and triazinyl ring structures. The aryl or heteroaryl substituents may be unsubstituted or substituted with one or more substituents selected from halogen, hydroxy, nitro, cyano, aryloxy, formyl, $C_1$-$C_6$ alkyl, $C_2$-$C_6$ alkenyl, $C_2$-$C_6$ alkynyl, $C_1$-$C_6$ alkoxy, halogenated $C_1$-$C_6$ alkyl, halogenated $C_1$-$C_6$ alkoxy, $C_1$-$C_6$ acyl, $C_1$-$C_6$ alkylthio, $C_1$-$C_6$ alkylsulfinyl, $C_1$-$C_6$ alkylsulfonyl, aryl, $C_1$-$C_6$OC(O)alkyl, $C_1$-$C_6$ NHC(O)alkyl, C(O)OH, $C_1$-$C_6$C(O)Oalkyl, C(O)NH$_2$, $C_1$-$C_6$ C(O)NHalkyl, or $C_1$-$C_6$ C(O)N(alkyl)$_2$, provided that the substituents are sterically compatible and the rules of chemical bonding and strain energy are satisfied.

The terms "arylalkyl" and "heteroarylalkyl" refer to $C_1$-$C_4$ alkyl groups substituted with one or more aryl or heteroaryl groups.

The compounds of this invention can exist as one or more stereoisomers. The various stereoisomers include geometric isomers, diastereomers and enantiomers. Thus the compounds of the present invention include racemic mixtures, individual stereoisomers and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials or by conventional resolution procedures.

The compounds of formula (I), wherein Het, X, $R^1$ through $R^5$, n and m are as previously defined can be prepared by the methods illustrated in Scheme A.

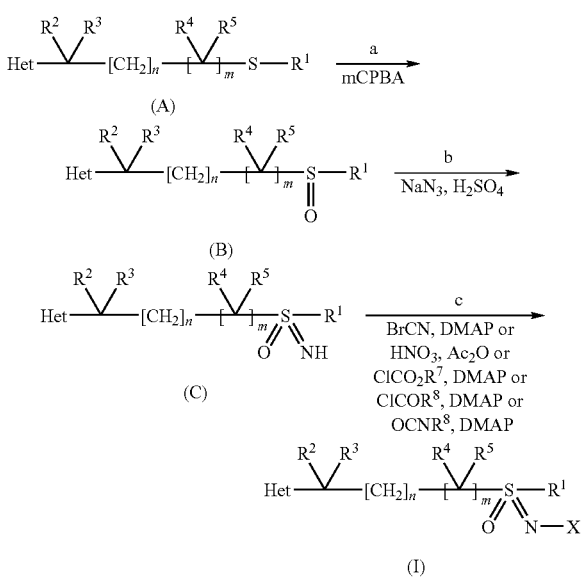

In step a of Scheme A, the sulfide of formula (A) is oxidized with meta-chloroperoxybenzoic acid (mCPBA) in a polar solvent below 0° C. to provide the corresponding sulfoxide. In most cases, dichloromethane is the preferred solvent for oxidation. In step b of Scheme A, the sulfoxide of formula (B) is iminated with sodium azide in the presence of concentrated sulfuric acid in an aprotic solvent under heating to provide the N-unsubstituted sulfoximine of formula (C). In most cases, chloroform is the preferred solvent for this reaction. Lastly, in step c of Scheme C, the sulfoximine nitrogen of formula (C) can be either cyanated with cyanogen bromide in the presence of a base, nitrated with nitric acid in the presence of acetic anhydride under mildly elevated temperature, carboxylated with alkyl ($R^4$) chloroformate in the presence of base such as 4-dimethylaminopyridine (DMAP), acylated with an acid chloride in the presence of base such as DMAP, or reacted with alkyl or acyl isocyanates in the presence of a base such as DMAP at ambient temperature to provide N-substituted sulfoximines of formula (I). Base is required for efficient cyanation, carboxylation, and acylation and the preferred base is DMAP, whereas sulfuric acid is used as catalyst for efficient nitration reaction.

The compounds of formula (I), wherein Het, X, $R^1$ through $R^5$, n and m are as previously defined can alternatively be prepared by the preferred method illustrated in Scheme B.

Scheme B

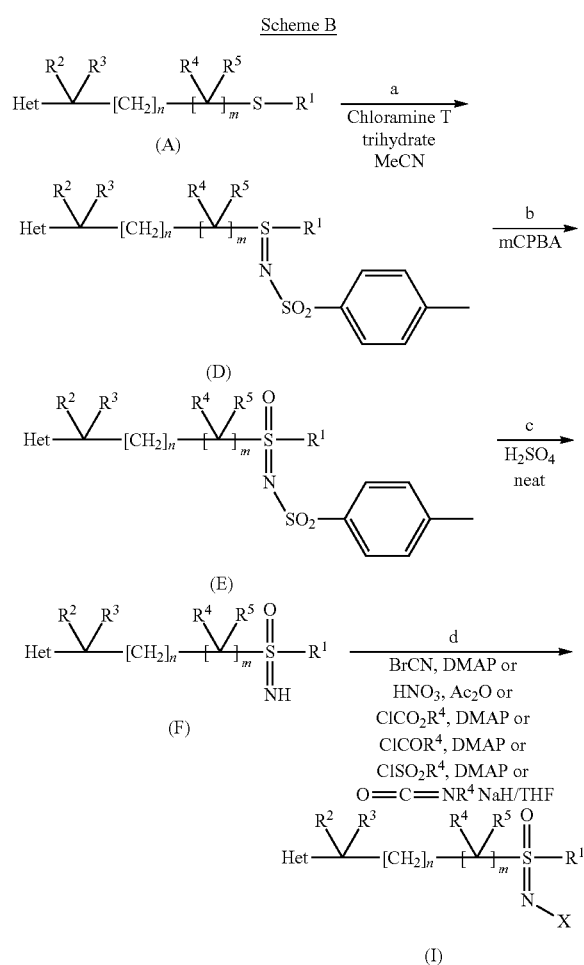

In step a of Scheme A, sulfide of formula (A) is iminated with chloramine T trihydrate a polar solvent at 60° C. to provide an N-tosylsulfilimine of formula (B). In most cases, acetonitrile is the preferred solvent for the imination.

In step b of Scheme A, N-tosylsulfilimine (B) is hydrolyzed in neat sulfuric acid to provide the N-unsubstituted sulfilimine (C). This product is typically used directly in the next reaction without further purification.

In step c of Scheme A, the nitrogen of sulfilimine (C) can be either cyanated with cyanogen bromide in the presence of a base, or nitrated with nitric acid in the presence of acetic anhydride under mildly elevated temperature, carboxylated with alkyl ($R^4$) chloroformate in the presence of base such as DMAP, acylated with either alkyl or aryl ($R^5$) acid chlorides in the presence of base such as DMAP, sulfonated with either alkyl or aryl sulfonyl chlorides in the presence of base such as DMAP, or reacted with alkyl or acyl isocyanates in the presence of a base such as at ambient temperature to provide N-substituted sulfoximine (I).

The compounds of formula (Ia) wherein X represents CN and Het, $R^1$-$R^5$, n and m are as previously defined, can be also be prepared by the mild and efficient method illustrated in Scheme C.

Scheme C

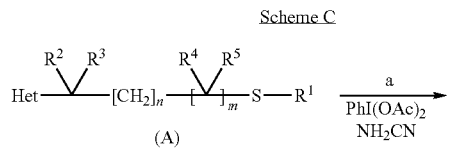

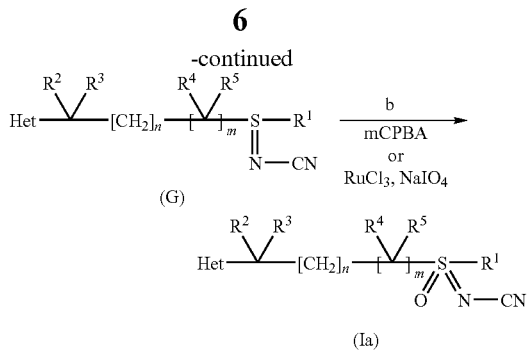

In step a of Scheme C, sulfides of formula (B) are oxidized with iodobenzene diacetate in the presence of cyanamide at 0° C. to give sulfilimine (G). The reaction can be carried out in a polar aprotic solvent like dichloromethane.

In step b of Scheme C, the sulfilimine (G) is oxidized with mCPBA. A base such as potassium carbonate is employed to neutralize the acidity of mCPBA. Protic polar solvents such as ethanol and water are used to increase the solubility of the sulfilimine starting material and the base employed. The sulfilimine (G) can also be oxidized with aqueous sodium or potassium periodinate solution in the presence of catalyst ruthenium trichloride hydrate or similar catalyst. The organic solvent for this catalysis can be polar aprotic solvent such as dichloromethane, chloroform, or acetonitrile.

The starting sulfides (A) in Schemes A, B, and C can be prepared in different ways as illustrated in Schemes D, E, F, G, H, I, and J.

Sulfides of formula ($A_1$) wherein m and n are 0, $R^3$ is H, and Het, $R^1$, and $R^2$ are as previously defined can be prepared either by nucleophilic substitution of the chloride or bromide of formula (J) with the sodium salt of an alkyl thiol or by the reaction of the alcohol (X=OH) of formula (J) with a disulfide in the presence of triphenyl phosphine as shown in Scheme D.

Scheme D

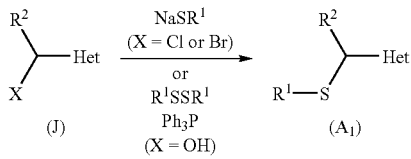

The sulfide of formula ($A_2$), wherein m and n=1, $R^3$, $R^4$ and $R^5$=H, and Het, $R^1$ and $R^2$ are as previously defined can be prepared by the methods illustrated in Scheme E. Accordingly, reaction of the chloride of formula (J) with dimethyl malonate in the presence of base such as potassium tert-butoxide provides a mono-substituted malonate, which is hydrolyzed under basic conditions to form a diacid. Decarboxylation of the diacid by heating gives a monoacid; reduction of the monoacid with borane-tetrahyrofuran complex provides the corresponding alcohol. Tosylation of the alcohol with toluenesulfonyl chloride (tosyl chloride) in the presence of a base like pyridine gives a tosylate and replacement of the tosylate with the sodium salt of the desired thiol provides sulfide ($A_2$).

Scheme E

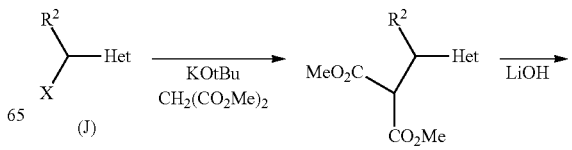

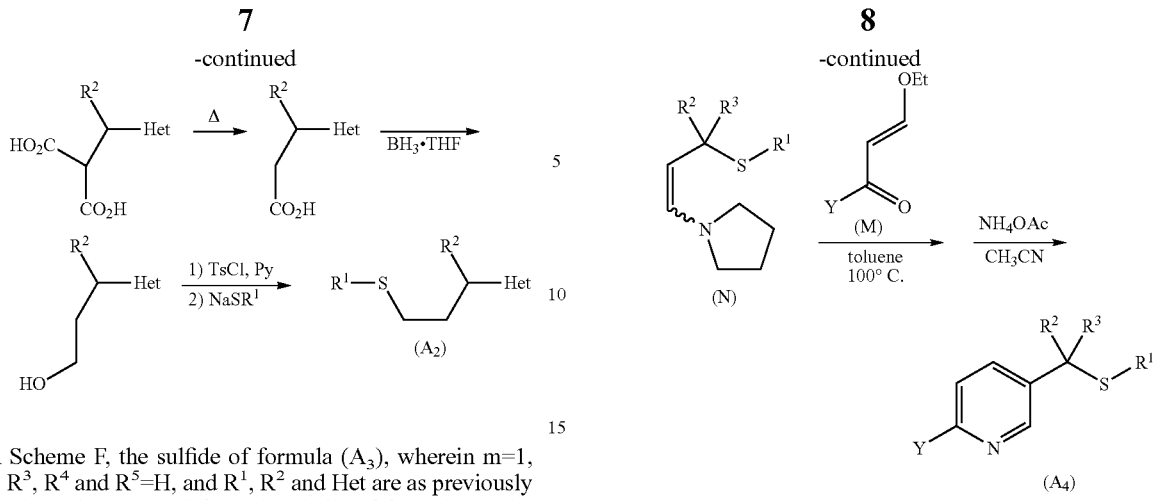

In Scheme F, the sulfide of formula (A₃), wherein m=1, n=0, $R^3$, $R^4$ and $R^5$=H, and $R^1$, $R^2$ and Het are as previously defined can be prepared from the nitrile of formula (K) by deprotonation with a strong base and alkylation with an alkyl iodide to give α-alkylated nitrile, hydrolysis of the α-alkylated nitrile in the presence of a strong acid like HCl to give an acid, reduction of the acid with borane-tetrahyrofuran complex to provide an alcohol, tosylation of the alcohol with tosyl chloride in the presence of a base like pyridine to give a tosylate and replacement of the tosylate with the sodium salt of the desired thiol.

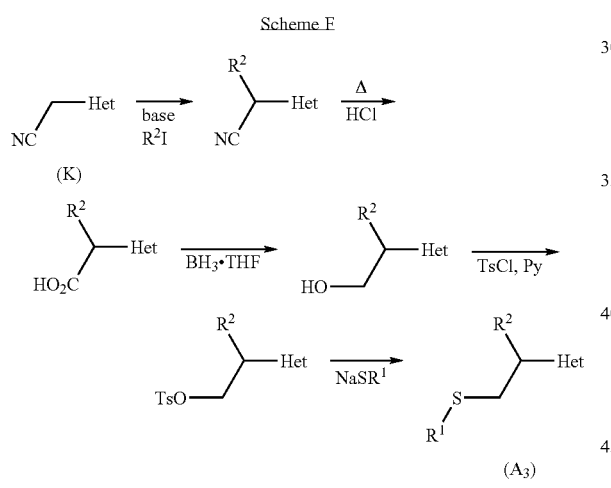

Pyridyl sulfides of formula (A₄) wherein m and n are 0, and $R^1$, $R^2$, and $R^3$ are as previously defined can be prepared according to the method illustrated in Scheme G wherein enamines (N), formed from the addition of an amine, e.g., pyrrolidine, with the Michael adduct of certain sulfides with appropriately substituted α,β-unsaturated aldehydes, are coupled with substituted enones (M) and cyclized with ammonium acetate in CH₃CN to yield the desired sulfide.

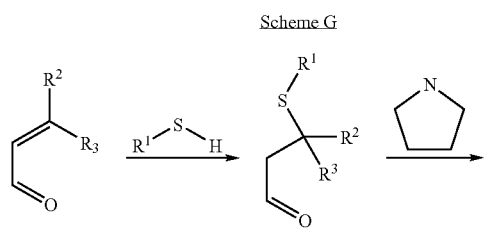

A variation of this method, illustrated in Scheme H, can be used to prepare cyclic pyridyl sulfides A₅ wherein n=1 or 2, m=0, $R^2$=H, and $R^1$ and $R^3$ are taken together to form a saturated 5- or -6 membered ring. Accordingly, reaction of either tetrahydrothiophen-3-one (n=1) or tetrahydrothiopyran-4-one (n=2) with triphenylphosphine and dimethylcarbonate provides the corresponding olefin, which is then hydroformylated with hydrogen and carbon monoxide in the presence of a rhodium catalyst at elevated pressure to afford aldehyde (N). Remaining steps to convert aldehyde (N) to sulfide (A₅) follows the same protocol as previously described in Scheme G.

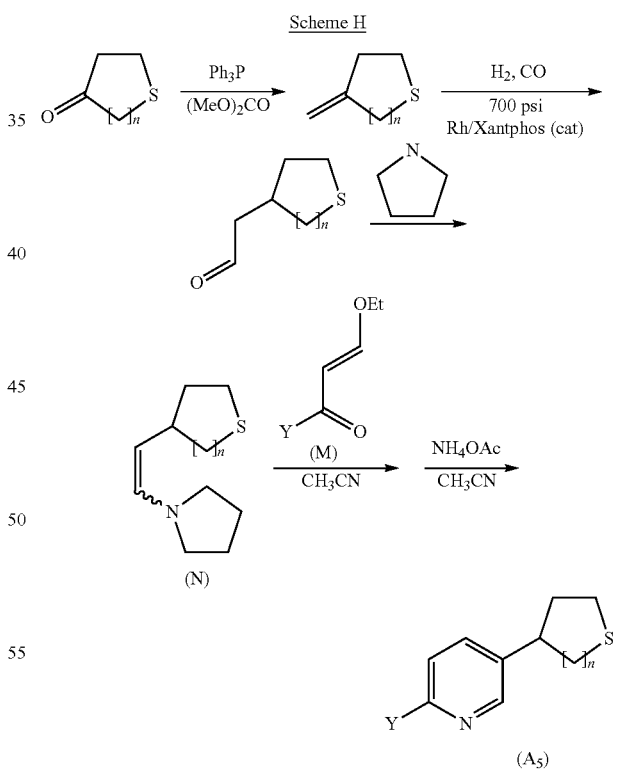

n = 1 or 2

In Scheme I, sulfides of formula (A₆) wherein $R^1$ and Y are as previously defined, m and n=1, $R^2$ and $R^5$=H, and $R^3$ is taken together with $R^4$ to form a saturated 5- or 6-membered ring can be prepared from 2-substituted 5-bromo-pyridines with a halogen metal exchange with isopropyl Grignard followed by conjugate addition to cyclic α,β-unsaturated ketones. Subsequent reduction of the ketone and conversion of the alcohol to the sulfide via methods described in Scheme D affords desired sulfides ($A_6$).

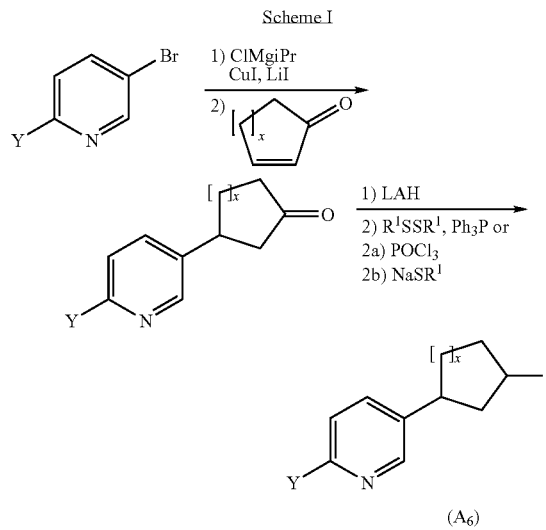

In Scheme J sulfides of formula ($A_6$) wherein $R^1$ and Y are as previously defined, m=1, n=0, $R^2$ and $R^5$=H, and $R^3$ is taken together with $R^4$ to form a saturated 5- or 6-membered ring can be prepared from 2-substituted 5-bromo-pyridines via a halogen metal exchange with either isopropyl Grignard or n-butyl lithium followed by addition to cyclic ketone such as cyclopentanone (x=1), dehydration to the olefin under acidic conditions, hydroboration (borane in tetrahydrofuran), oxidative cleavage (sodium hydroxide and hydrogen peroxide), conversion of the resulting alcohol to a easily displaceable moiety such as a methanesulfonyl group (by treatment with methanesulfonyl chloride and triethyl amine), and finally nucleophilic substitution with the sodium salt of an alkyl thiol.

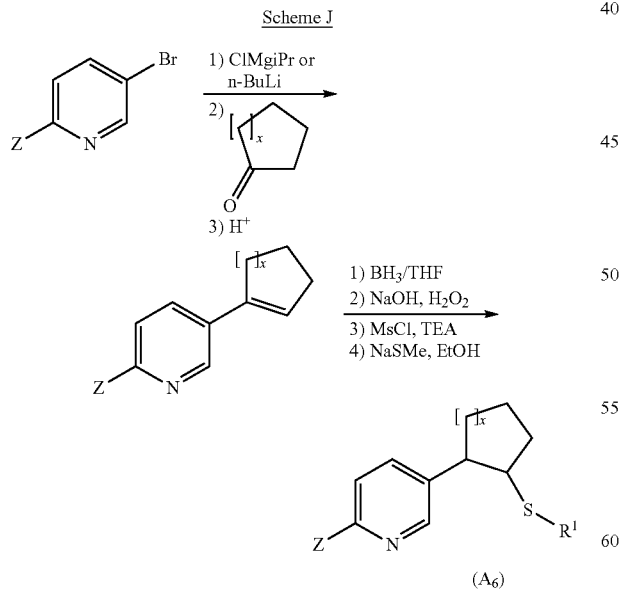

In certain cases it is advantageous to prepare sulfoximines of formula (I) from other sulfoximines. These methods are illustrated in Schemes K, L, and M.

In Scheme K, sulfoximines of formula (Ic) wherein $R^1$, Het, and X are as previously defined, n and m=0, and $R^2$ is $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxyalkyl, $C_1$-$C_4$ haloalkoxy $C_1$-$C_4$ alkyl, $COOR^7$, $COR^8$, and $CONR^7R^8$ can be prepared from unsubstituted sulfoximines of formula (Ib) by deprotonation of the α-carbon in the presence of a base such as potassium hexamethyldisilamide (KHMDS) and reaction with a wide variety of electrophiles including, but not limited to, alkyl halides (X=halogen), alkyl and aryl anhydrides or acid chlorides (X=$CO_2R'$ or Cl), alkyl or aryl chloroformates, isocyanates, α,β-unsaturated ketones, and epoxides.

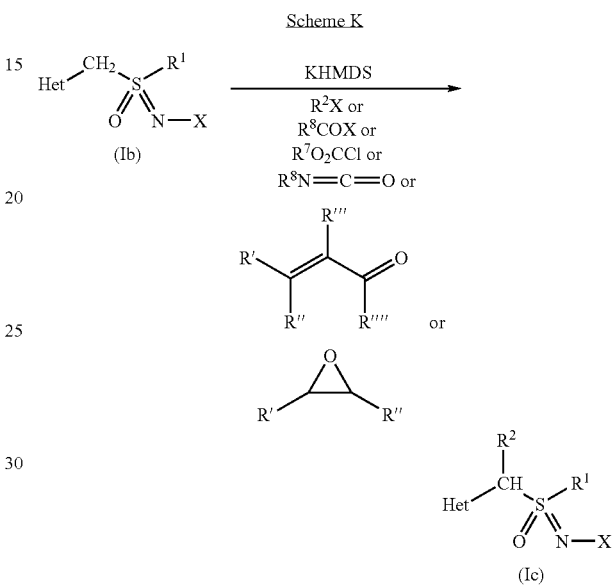

Sulfoximines of formula (Ic) can be further alkylated under conditions analogous to those described in Scheme K to provide (disubstituted)methyl sulfoximines of formula (Id) wherein and $R^1$, Het, and X are as previously defined and $R^2$ and $R^3$ independently represent $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, alkoxyalkyl, haloalkoxyalkyl, $COOR^7$, $COR^8$, and $CONR^7R^8$ as illustrated in Scheme L.

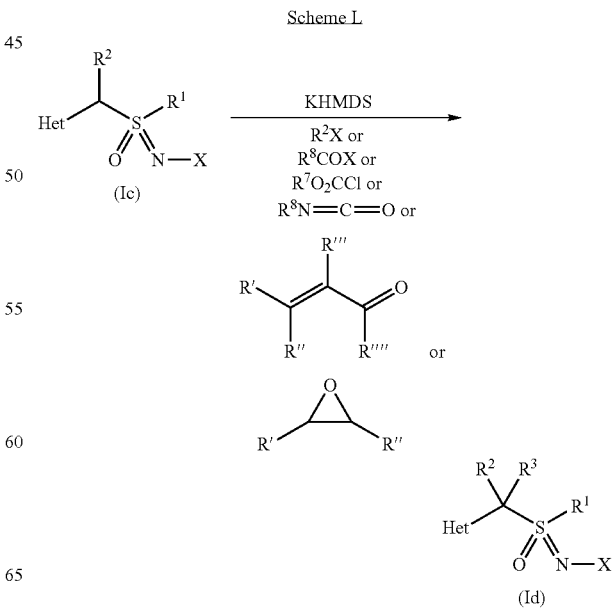

In Scheme M, cyclic sulfoximines of formulas (Ie), (If), (Ig), and (Ih), wherein $R^1$ and $R^4$ are take together to form a 4- or 5-membered ring (p=1 or 2), are obtained from sulfoximine (Q) which in turn is prepared from either tetrahydrothiophene (p=1) or pentamethylene sulfide (p=2) according to the conditions described above in Schemes A-C. Deprotonation of (Q) with a strong base, preferably n-butyl lithium, followed by reaction with either chloro methyl heterocycles of formula (J), Weinreb amides (R), epoxides (S), or ketones (T), provides substituted sulfoximes of formulas (Ie), (If), (Ig; m=1), and (Ig; m=0) respectively. The alcohol of (Ig) can be further modified to form alkoxides (Ih) by reaction with alkyl iodides in the presence of a base such as potassium t-butoxide.

Scheme M

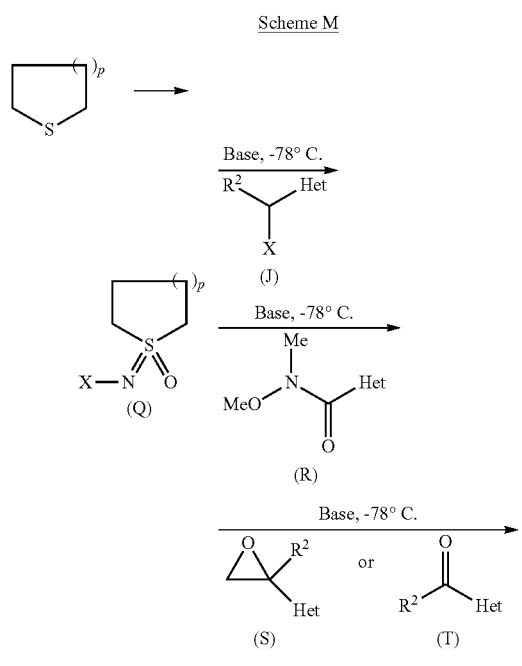

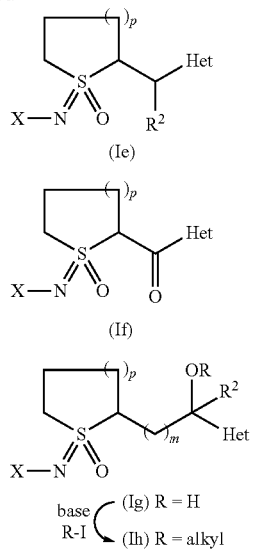

Intermediates (J), (R), (S), and (T) described in Scheme M wherein Het is a substituted pyridine and Y is either alkyl or haloalkyl can be prepared according to the methods illustrated in Scheme N. Thus, dimethylaminoacrylonitrile is coupled with enone (M) and cyclized with ammonium acetate in DMF to yield the corresponding 6-substituted nicotinonitrile. Treatment with an alkyl or aryl-magnesium bromide affords ketone ($T_1$). Alternatively ketone ($T_1$) can be obtained from the coupling of dimethylamino vinyl ketones with enone (M) followed by cyclization with ammonium acetate in DMF. Reduction of ($T_1$) with sodium borohydride and chlorination with thionyl chloride provides chloromethyl pyridines ($J_1$). Reaction of ($T_1$) with the anion of trimethylsulfoxonium iodide affords epoxide ($S_1$). Hydrolysis of nicotinonitrile to the corresponding carboxylic acid followed by treatment with 1,1'-carbonyldiimidazole and subsequent reaction with N,O-dimethylhydroxylamine affords Weinreb amide ($R_1$).

Scheme N

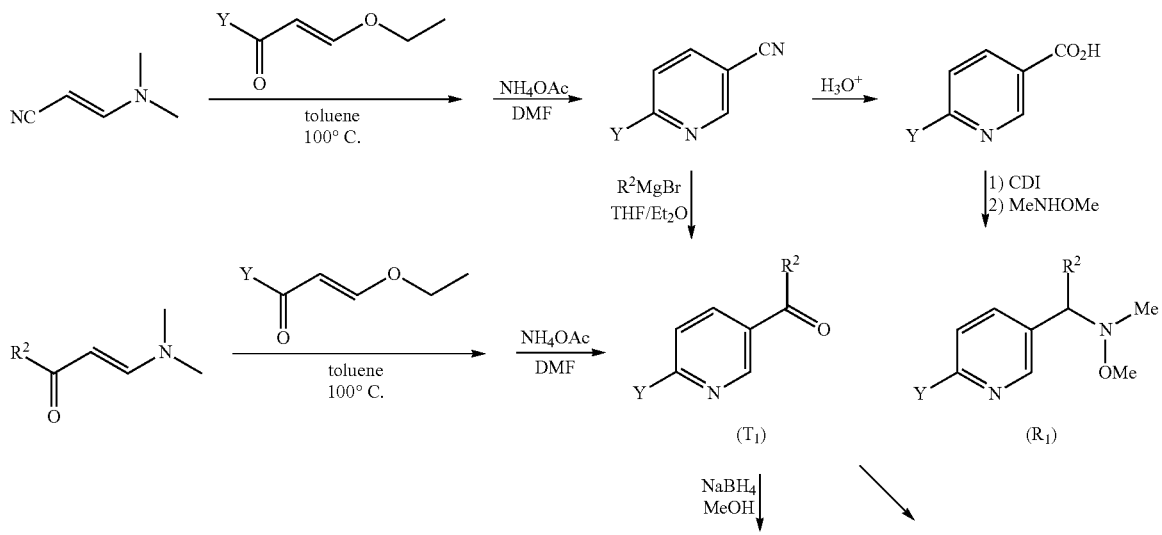

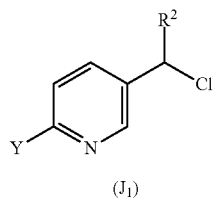

(J₁)

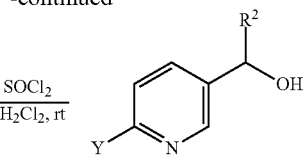

-continued

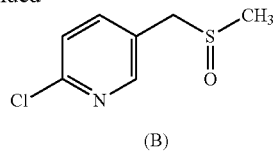

(S₁)

EXAMPLES

Example I

Preparation of [1-(6-chloropyridin-3-yl)-2-(1,3-thiazol-4-yl)ethyl](methyl)oxido-$\lambda^4$-sulfanylidenecyanamide (1)

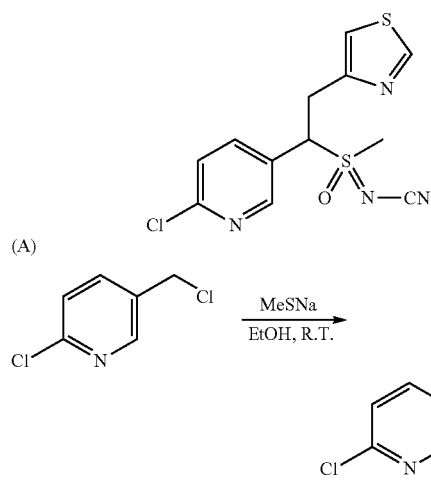

(A)

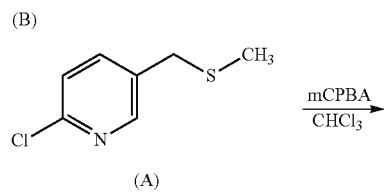

(A)

A solution of 5-chloromethyl-2-chloropyridine (8.1 g, 50 mmol) in ethanol (50 mL) was added to a suspension of sodium thiomethoxide solid (4.2 g, 60 mmol) in 100 mL ethanol under stirring. An exothermic reaction was observed during the addition and the mixture was then stirred at room temperature overnight. The solvent ethanol was removed under reduced pressure and the residue was re-dissolved in ether-EtOAc solvent and mixed with brine. The two phases were separated and the organic layer was dried over anhydrous $Na_2SO_4$, filtered, concentrated and purified by eluting through a silica gel plug with 40% EtOAc in hexane to give 8.14 g of 2-chloro-5-[(methylthio)methyl]pyridine (A) as a colorless oil in 94% yield. The product was analytically pure and directly used for the next step reaction. $^1$H NMR (300 MHz, $CDCl_3$) δ 8.28 (dd, 1H), 7.65 (dd, 1H), 7.30 (d, 1H), 3.63 (s, 2H), 2.00 (s, 3H).

(B)

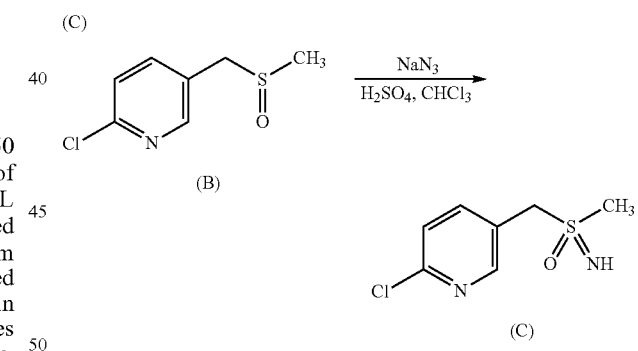

To a solution of 2-chloro-5-[(methylthio)methyl]pyridine (A) (7.60 g, 40 mmol) in chloroform (100 mL) cooled in ice-water bath was added a solution of 70-75% m-chloroperbenzoic acid (mCPBA, 10.51 g, ca 44 mmol) in chloroform (110 mL) over a period of 1.5 h under stirring. The stirring was continued for another 1 h at 0° C. Methanol (12 mL) was added to the mixture, which was then bubbled with ammonia gas to precipitate the benzoic acid and the extra mCPBA if any. TLC showed there was small amount of unreacted starting material in the reaction mixture. Most of the ammonium salt was removed by filtration. The filtrate was concentrated before it was loaded onto a $Et_3$N-treated silica gel plug, which was eluted with 10% MeOH in $CH_2Cl_2$ to give 7.6 g of 2-chloro-5-[(methylsulfinyl)methyl]pyridine (B) in 92% yield as a colorless oil that turned into a white solid upon drying in vacuo (m.p. 72-74° C.). LC-MS (ELSD): mass calcd for $C_7H_8ClNOS$ $[M+H]^+$ 190.67. Found: 190.21.

To a stirred mixture of 2-chloro-5-[(methylsulfinyl)methyl]pyridine (B) (7.34 g, 39 mmol) and sodium azide (4.04 g, 62 mmol) in chloroform (80 mL) cooled to 0° C. was slowly added sulfuric acid at a rate such that the temperature did not rise above 8° C. After the addition was over, the ice-water bath was removed and the mixture was heated at 55° C. for 2.5 h. The solvent was decanted into a separation funnel and the residue was stirred and dissolved in water. After a few minutes, the aqueous mixture was made basic to pH 8 by slowly adding solid $Na_2CO_3$ and then saturated with solid NaCl. The extra salt was removed by filtration (a portion of the filtrate was sucked into trap and was not recovered) and the filtrate was extracted with $CH_2Cl_2$ three times. The combined organic layer was dried over $Na_2SO_4$, filtered, concentrated and the residue was triturated in $CH_2Cl_2$-ether (1:10, v/v) solvent. The white solid was filtered, washed with $CH_2Cl_2$- ether (1:10, v/v) and dried to give 2.70 g of -chloro-5-[(methylsulfonimidoyl)methyl]pyridine (C) in 34% yield as a white solid (m.p. 134.5-136° C.). LC-MS (ELSD): mass calcd for $C_7H_9ClN_2OS$ $[M+H]^+$ 203.67. Found: 203.22.

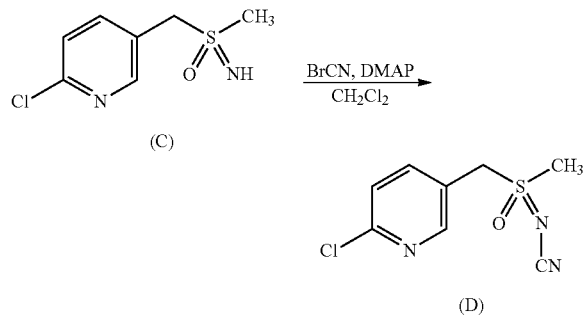

To a stirred mixture of -chloro-5-[(methylsulfonimidoyl)methyl]pyridine (C) (2.04 g, 10 mmol) and 4-dimethylaminopyridine (DMAP, 1.22 g, 10 mmol) in $CH_2Cl_2$ (15 mL) was added cyanogen bromide (5.0 mL, 15 mmol). An exothermic reaction was observed. The resulting solution was stirred at room temperature for 2 h and quenched with 2 N aqueous HCl solution. After separation of the two phases, the aqueous layer was extracted with $CH_2Cl_2$ three times. The combined organic layer was dried over $Na_2SO_4$, filtered, concentrated, and purified on silica gel using 5% MeOH in $CH_2Cl_2$ as eluent to give 1.51 g of [(6-chloropyridin-3-yl)methyl](methyl)oxido-$\lambda^4$-sulfanylidenecyanamide (D) in 66% yield as a greenish oil which turned into a greenish solid while being dried under vacuum (m.p. 115-117° C.). $^1H$ NMR (300 MHz, $CDCl_3+CD_3OD$) δ 8.49 (d, 1H), 7.96 (dd, 1H), 7.55 (d, 1H), 4.98 (s, 2H), 3.40 (s, 3H). $^{13}C$ NMR (300 MHz, $CDCl_3+CD_3OD$) δ 153.6, 152.7, 143.2, 125.8, 123.1, 113.2, 57.86, 39.97. LC-MS (ELSD): mass calcd for $C_8H_8ClN_3OS$ $[M-H]^+$ 228.68. Found. 228.19.

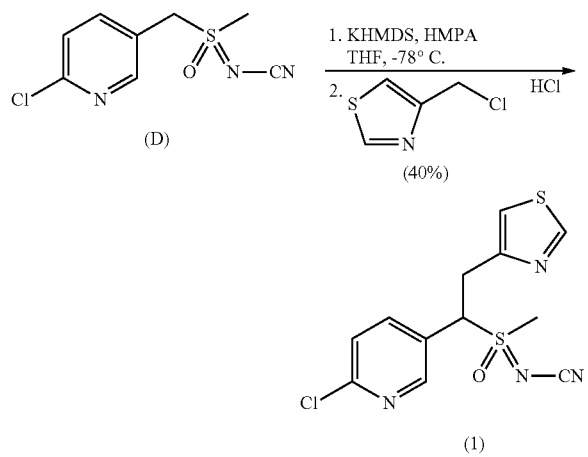

To a solution of [(6-chloropyridin-3-yl)methyl](methyl)oxido-$\lambda^4$-sulfanylidenecyanamide (D) (300 mg, 1.3 mmol) and hexamethylphosphoramide (HMPA; 113 μL, 0.65 mmol) in tetrahydrofuran (THF, 5 mL) at −78° C. was added potassium hexamethyldisilazane (KHMDS; 0.5 M in toluene, 2.9 mL, 1.4 mmol) dropwise. The solution was stirred at −78° C. for 20 min, after which 4-(chloromethyl)thiazole hydrochloride (244 mg, 1.4 mmol) was added slowly as a solution in THF (2 mL). The reaction was allowed to warm to room temperature over the course of 2 h, then the reaction was quenched with satd aq $NH_4Cl$ and extracted with $CH_2Cl_2$ (3×). The organic layer was dried over $MgSO_4$, concentrated, and the crude product purified by flash chromatography to furnish sulfoximine (1) as a light brown oil in 40% yield as a 55:45 mixture of diastereomers. $^1H$ NMR (400 MHz, $CDCl_3$) δ (major diastereomer) 8.72 (d, 1H), 8.36 (d, 1H), 7.91 (dd, 1H), 7.41 (d, 1H), 7.07 (s, 1H), 5.20 (m, 1H), 4.06 (dd, 1H), 3.67 (dd, 1H), 3.07 (s, 3H); (minor diastereomer) 8.72 (d, 1H), 8.36 (d, 1H), 7.86 (dd, 1H), 7.40 (d, 1H), 7.07 (s, 1H), 5.20 (m, 1H), 4.06 (dd, 1H), 3.63 (dd, 1H), 3.05 (s, 3H): LC-MS (ELSD): Exact mass calcd for $C_{12}H_{12}ClN_4OS_2$ $[M+H]^+$, 327. Found 327.

Example II

Preparation of {1-[6-(trifluoromethyl)pyridin-3-yl]-2-(cyclopropyl)ethyl}(methyl)oxido-$\lambda^4$-sulfanylidenecyanamide (2)

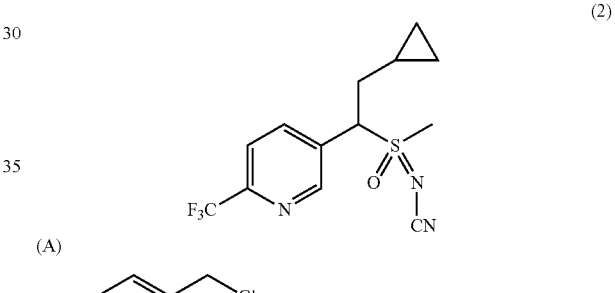

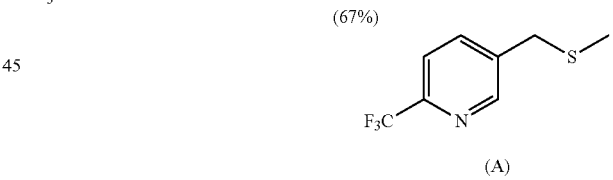

To a solution of 3-chloromethyl-6-(trifluoromethyl)pyridine (5.1 g, 26 mmol) in dimethyl sulfoxide (DMSO; 20 mL) was added in one portion sodium thiomethoxide (1.8 g, 26 mmol). A violent exothermic reaction was observed which resulted in the reaction turning dark. The reaction was stirred for 1 hr, then additional sodium thiomethoxide (0.91 g, 13 mmol) was added slowly. The reaction was stirred overnight, after which it was poured into $H_2O$ and several drops of conc. HCl were added. The mixture was extracted with $Et_2O$ (3×50 mL) and the organic layers combined, washed with brine, dried over $MgSO_4$ and concentrated. The crude product was purified by chromatography (Prep 500, 10% acetone/hexanes) to furnish the sulfide (A) as a pale yellow oil (3.6 g, 67%). $^1H$ NMR (300 MHz, $CDCl_3$) δ 8.6 (s, 1H), 7.9 (d, 1H), 7.7 (d, 1H), 3.7 (s, 2H), 2.0 (s, 3H); GC-MS: mass calcd for $C_8H_8F_3NS$ $[M]^+$ 207. Found 207.

(B)

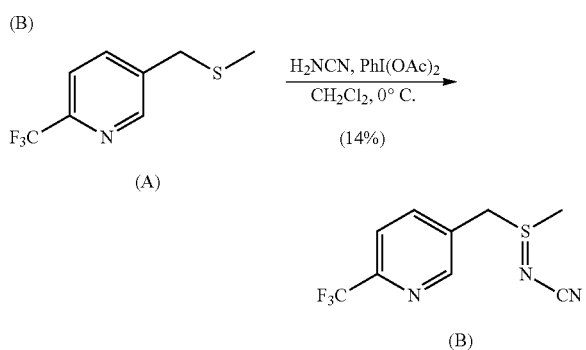

(D)

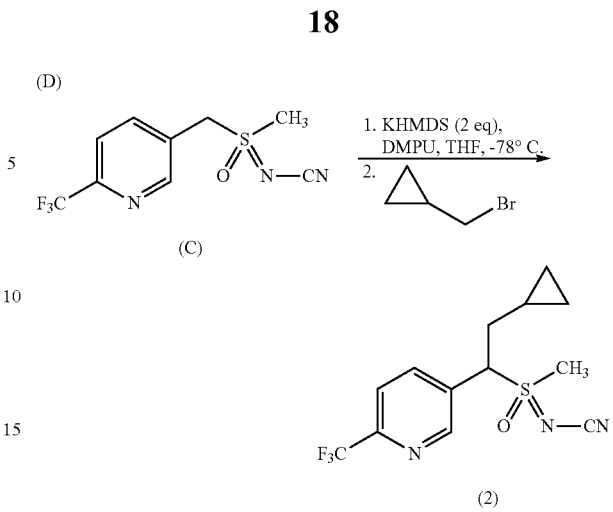

To a solution of sulfide (A) (3.5 g, 17 mmol) and cyanamide (1.4 mg, 34 mmol) in CH$_2$Cl$_2$ (30 mL) at 0° C. was added iodobenzenediacetate (11.0 g, 34 mmol) all at once. The reaction was stirred for 30 min, then allowed to warm to room temperature overnight. The mixture was diluted with CH$_2$Cl$_2$ (50 mL) and washed with H$_2$O. The aqueous layer was extracted with ethyl acetate (4×50 mL), and the combined organic layers were dried over MgSO$_4$ and concentrated. The crude product was triturated with hexanes and purified by chromatography (chromatotron, 60% acetone/hexanes) to furnish the sulfilimine (B) as a yellow gum (0.60 g, 14%). IR (film) 3008, 2924, 2143, 1693 cm$^{-1}$; $^1$H NMR (300 MHz, CDCl$_3$) δ 8.8 (s, 1H), 8.0 (d, 1H), 7.8 (d, 1H), 4.5 (d, 1H), 4.3 (d, 1H), 2.9 (s, 3H); LC-MS (ESI): mass calcd for C$_9$H$_9$F$_3$N$_3$S [M+H]+ 248.04. Found 248.

(C)

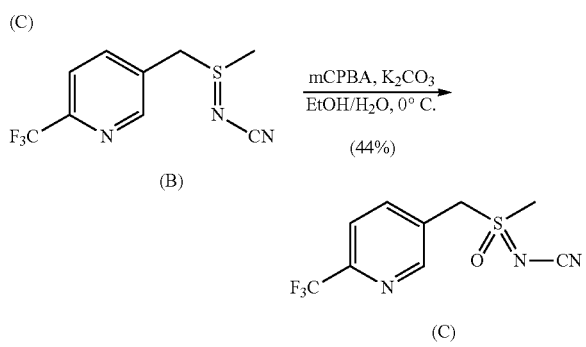

To a solution of mCPBA (80%, 1.0 g, 4.9 mmol) in EtOH (10 mL) at 0° C. was added a solution of K$_2$CO$_3$ (1.4 g, 10 mmol) in H$_2$O (7 mL). The solution was stirred for 20 min, then a solution of sulfilimine (B) (0.60 g, 2.4 mmol) in EtOH (20 mL) was added all at once. The reaction was stirred at 0° C. for 30 min, then allowed to warm to room temperature over the course of 1 hr. The reaction was then quenched with aq. sodium bisulfite and the mixture was concentrated to remove ethanol. The resulting mixture was extracted with CH$_2$Cl$_2$ and the combined organic layers dried over MgSO$_4$ and concentrated. The crude product was purified by chromatography (chromatotron, 50% acetone/hexanes) to furnish [(6-trifluoromethylpyridin-3-yl)methyl](methyl)-oxido-λ$^4$-sulfanylidenecyanamide (C) as an off-white solid (0.28 g, 44%). Mp=135-137° C.; $^1$H NMR (300 MHz, CDCl$_3$) δ 8.8 (s, 1H), 8.1 (d, 1H), 7.8 (d, 1H), 4.7 (m, 2H), 3.2 (s, 3H); LC-MS (ELSD): mass calcd for C$_9$H$_9$F$_3$N$_3$OS [M+H]$^+$ 264.04. Found 263.92.

To a solution of [(6-trifluoromethylpyridin-3-yl)methyl](methyl)-oxido-λ$^4$-sulfanylidenecyanamide (C) (0.500 g, 1.90 mmol) in THF (15 mL), DMPU (0.122 mL, 0.950 mmol) was added at room temperature. The solution was cooled to −78° C. Next, KHMDS (4.18 mL of 0.5M solution in toluene, 2.09 mmol) was added dropwise to the reaction mixture. The reaction was allowed to stir for 20 mins. Next, cyclopropylmethyl bromide (0.230 mL, 2.09 mmol) was added dropwise. Following addition, the reaction was allowed to warm to rt over a 2 h period. Upon completion of reaction, the mixture was quenched with sat'd. NH$_4$Cl (aq) and extracted with CH$_2$Cl$_2$. The organics were combined, dried over anhydrous Na$_2$SO$_4$, and concentrated in vacuo. The crude product was purified using reverse-phase HPLC to give title compound (2) as a mixture of diastereomers (yellow oil; 0.163 g. 27%). $^1$H NMR (300 MHz, CDCl$_3$) δ8.60 (s, 1H), 7.96 & 7.92 (m, 1H), δ7.64 & 7.62 (m, 1H), 4.41 & 4.38 (m, 1H), 2.86 & 2.83 (s, 3H), 2.31 & 1.94 (m, 2H), 0.29 & −0.01 (m, 2H); LC-MS (ELSD): mass calcd for C$_{13}$H$_{14}$F$_3$N$_3$OS 317.00. found [M+H] 318.01, [M−H] 316.04.

Example III

Preparation of cis-[2-(6-chloropyridin-3-yl)cyclopentyl](methyl)oxido-λ$^4$-sulfanylidenecyanamide (3)

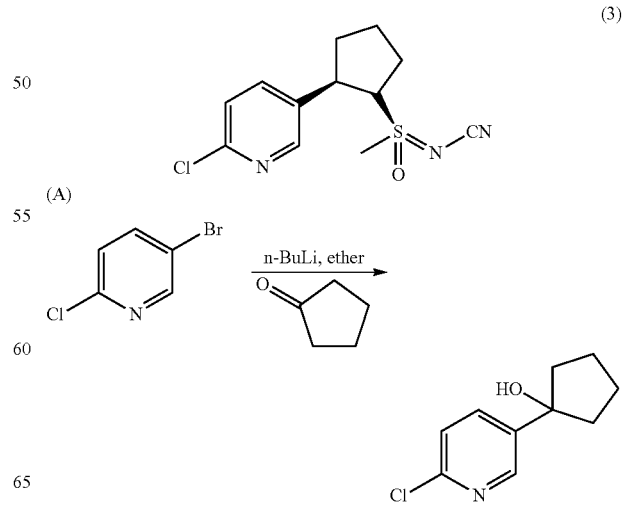

5-Bromo-2-chloropyridine (3.0 g, 15.6 mmol) was dissolved in diethyl ether (100 mL) in an oven-dried, nitrogen-flushed 250 mL round bottomed flask and cooled in a dry ice/acetone bath under nitrogen. n-BuLi (1.05 g, 16.4 mmol, 6.6 mL of a 2.5 M solution in hexanes) was added via syringe and the orange heterogenous mixture allowed to stir for 1 hour. Cyclopentanone (1.3 g, 15.6 mmol) was added via syringe and the mixture allowed to warm to −20° C. before being quenched with 1N HCl. The mixture was extracted with EtOAc and the organic extract washed with sat. NaHCO$_3$. The NaHCO$_3$ wash was used to neutralize the first aqueous layer and the combined aqueous layers were extracted with additional EtOAc and the combined organic layers dried (Na$_2$SO$_4$), filtered, concentrated and purified by flash silica gel chromatography (hexanes:EtOAc; 2:1) to give 1-(6-chloro-pyridin-3-yl)cyclopentanol (2.33 g, 76%) as an off white solid: mp 92-93° C., LC/MS (ESI) m/z 197, $^1$H NMR (300 MHz, CDCl$_3$) δ 8.50 (d, 1H, J=2.4 Hz), 7.77 (dd, 1H, J=8.4, 2.4 Hz), 7.28 (d, 1H, J=8.4 Hz), 2.05-1.80 (m, 8H), 1.60 (s, 1H, OH).

(B)

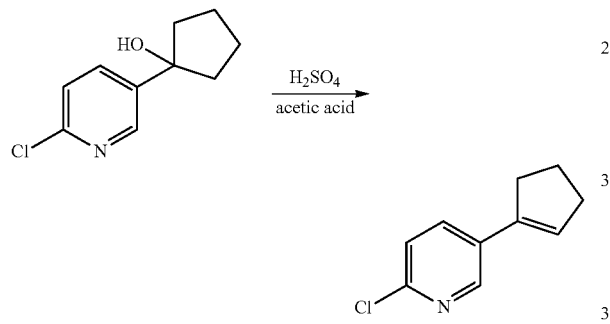

1-(6-Chloro-pyridin-3-yl)cyclopentanol (2.1 g, 10.5 mmol) was treated with acetic acid (12 mL) and sulfuric acid (4 mL) and the mixture heated to reflux for 30 min. After cooling to RT, ice and 2 N NaOH (180 mL) was add and the resulting tan precipitate collected by filtration, washed with H$_2$O and dried giving 2-chloro-5-(cyclopent-1-enyl)pyridine (1.66 g, 88%) as a tan solid: mp 59-60° C., LC/MS (ESI) m/z 179, $^1$H NMR (300 MHz, CDCl$_3$) δ 8.41 (d, 1H, J=2.4 Hz), 7.66 (dd, 1H, J=8.4, 2.4 Hz), 7.25 (d, 1H, J=8.4 Hz), 6.27 (t, 1H, J=2.1 Hz), 2.69 (bm, 2H), 2.55 (bm, 2H), 2.05 (m, 2H).

(C)

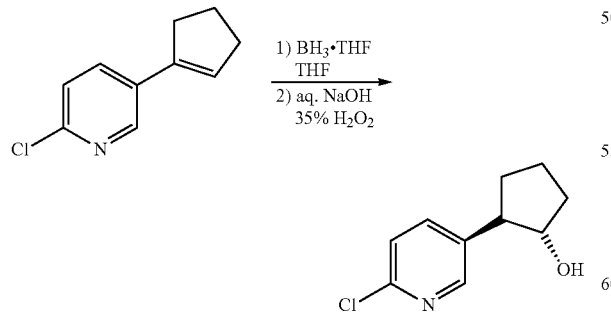

2-Chloro-5-(cyclopent-1-enyl)pyridine (1.5 g, 8.5 mmol) was dissolved in THF (30 mL) in an oven-dried, nitrogen-flushed 250 mL round bottom flask and the resulting solution cooled in a dry ice/acetone bath under nitrogen. BH$_3$.THF complex (2.4 g, 28.0 mmol, 28 mL of a 1 M solution in THF) was added dropwise with stirring via syringe and the mixture was allowed to warm slowly to room temperature and stir overnight. 2 N NaOH (15 mL), ethanol (15 mL) and 35% H$_2$O$_2$ (10 mL) were added and the mixture stirred for 0.5 h then diluted with EtOAc and 1 N HCl. The layers were separated and the organic layer washed with brine and aq. NaHSO$_3$, dried over Na$_2$SO$_4$, filtered through celite and concentrated. Purification by flash chromatography (hexanes: EtOAc/10:1→2:1) gave in order of elution by-products 2-chloro-5-cyclopentylpyridine (0.45 g, 29%) and 1-(6-chloropyridin-3-yl)-cyclopentanol (0.44 g, 26%) followed by the desired product trans-2-(6-chloropyridin-3-yl)cyclopentanol (0.25 g, 15%) as a clear oil: LC/MS (ESI) m/z 197, $^1$H NMR (300 MHz, CDCl$_3$) δ 8.26 (d, 1H, J=2.4 Hz), 7.55 (dd, 1H, J=8.4, 2.4 Hz), 7.25 (d, 1H, J=8.4 Hz), 4.12 (m, 1H), 2.88 (m, 1H), 2.24-1.62 (m, 6H).

(D)

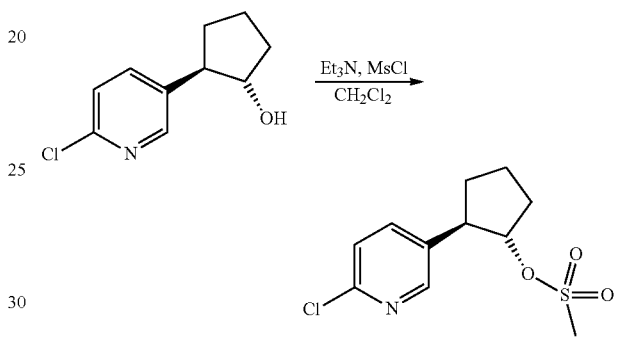

trans-2-(6-Chloropyridin-3-yl)cyclopentanol (0.225 g, 1.14 mmol) was dissolved in CH$_2$Cl$_2$ (10 mL) in a 50 mL round bottom flask, the solution cooled in an ice bath under nitrogen and treated with Et$_3$N (0.172 g, 1.71 mmol, 0.24 mL) and methanesulfonyl chloride (0.163 g, 1.42 mmol, 0.11 ml) via syringe with stirring. After 1 h, TLC (hexanes:EtOAc/2:1) indicated a complete conversion. The reaction mixture was concentrated in vacuo then partitioned between EtOAc and 1 N HCl, the layers separated, the organics dried (Na$_2$SO$_4$) filtered and concentrated to give trans-methanesulfonic acid 2-(6-chloropyridin-3-yl)cyclopentyl ester (0.303 g, 97%) as an oil: LC/MS (ESI) m/z 275, $^1$H NMR (300 MHz, CDCl$_3$) δ 8.28 (d, 1H, J=2.7 Hz), 7.56 (dd, 1H, J=8.1, 2.7 Hz), 7.3 (d, 1H, J=8.1 Hz), 4.93 (apparent q, 1H, J=5.7 Hz), 3.28 (apparent q, 1H, J=8.7 Hz), 2.86 (s, 3H), 2.26 (m, 2H), 2.10-1.80 (m, 3H), 1.73 (m, 1H).

(E)

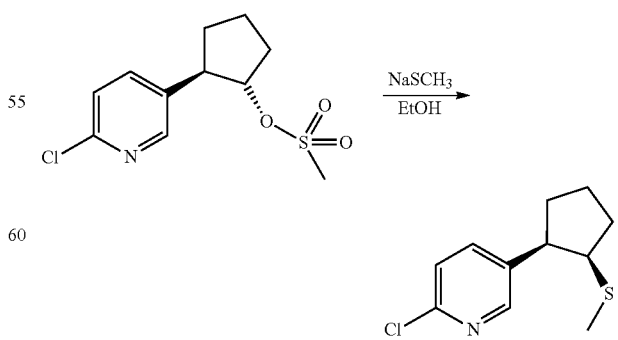

trans-Methanesulfonic acid 2-(6-chloropyridin-3-yl)cyclopentyl ester (0.295 g, 1.07 mmol) was dissolved in EtOH (5 mL) in a 25 mL round bottom flask and cooled in an ice bath under nitrogen. Sodium methane thiolate (0.224 g, 3.20 mmol) was added all at once and the cloudy white mixture was allowed to warm to room temperature and stir overnight. The mixture was diluted with EtOAc and brine and the layers separated. The organic layer was washed with brine, dried (Na$_2$SO$_4$), filtered, and concentrated. Purification by flash silica gel chromatography (hexanes:EtOAc/10:1) gave cis-2-chloro-5-(2-methylthiocyclopentyl)pyridine (0.148 g, 61%) as an oil: LC/MS (ESI) m/z 227, $^1$H NMR (300 MHz, CDCl$_3$) δ 8.27 (d, 1H, J=2.7 Hz), 7.60 (dd, 1H, J=8.1, 2.7 Hz), 7.26 (d, 1H, J=8.1 Hz), 3.30 (m, 2H), 2.24 (m, 1H), 2.15-1.65 (m, 5H), 1.74 (s, 3H).

(F)

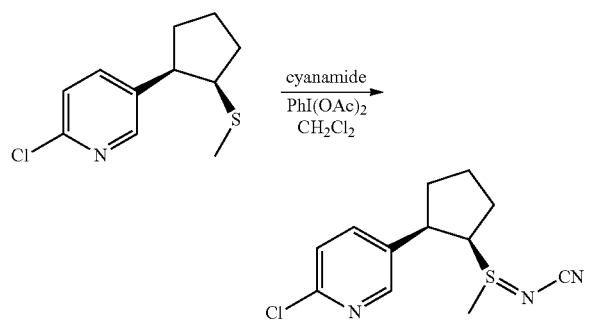

cis-2-Chloro-5-(2-methylthiocyclopentyl)pyridine (0.15 g, 0.64 mmol) was dissolved in CH$_2$Cl$_2$ (3 mL) in a 50 mL round bottom flask and treated with cyanamide (0.035 g, 0.83 mmol). The mixture was cooled in an ice bath under nitrogen and treated with iodobenzene diacetate (0.28 g, 0.86 mmol) and allowed to stir for 2 h by which time the reaction was judged complete by TLC (CH$_2$Cl$_2$:MeOH/20:1). The reaction mixture was concentrated to low volume and purified by flash silica gel chromatography (CH$_2$Cl$_2$:MeOH/20:1) to give cis-[2-(6-chloropyridin-3-yl)cyclopentyl](methyl)-λ$^4$-sulfanylidenecyanamide (0.145 g, 85%) as an oily 1:1 mixture of diastereomers: LC/MS (ESI) m/z 267, $^1$H NMR (300 MHz, CDCl$_3$) δ 8.31 (d, 2H, J=2.7 Hz), 7.70 (dd, 1H, J=8.4, 2.7 Hz), 7.63 (dd, 1H, J=8.4, 2.7 Hz), 7.40 (d, 1H, J=8.4 Hz), 7.32 (d, 1H, J=8.4 Hz), 3.96 (m, 1H), 3.81 (m, 1H), 3.67-3.51 (m, 2H), 2.73 (s, 3H), 2.59 (m, 1H), 2.45 (s, 3H), 2.40-1.95 (m, 9H), 1.85 (m, 2H).

(G)

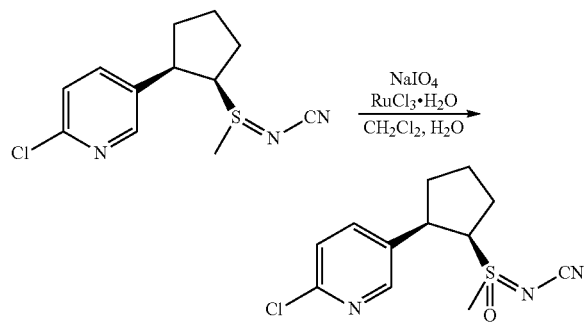

Sodium periodate (0.17 g, 0.78 mmol) was dissolved in water (2 mL) in a 50 L round bottom flask and mixed with cis-[2-(6-chloropyridin-3-yl)cyclopentyl](methyl)-λ$^4$-sulfanylidenecyanamide (0.11 g, 0.39 mmol) in CH$_2$Cl$_2$ (5 mL) and the bi-phasic mixture treated with ruthenium(III) chloride hydrate (0.004 g, 0.02 mmol) with vigorous stirring. Analysis of the dark reaction mixture by TLC (CH$_2$Cl$_2$: MeOH/20:1) indicated the complete consumption of starting material within 1.5 h. Charcoal was added to the reaction mixture which was stirred an additional 30 min before being filtered through celite with water and CH$_2$Cl$_2$. The organic layer was separated, dried (Na$_2$SO$_4$), filtered, and concentrated to give cis-[2-(6-chloropyridin-3-yl)cyclopentyl](methyl)oxido-λ$^4$-sulfanylidenecyanamide (0.08 g, 88%) as an oily mixture of diastereomers: LC/MS (ESI) m/z 283, $^1$H NMR (300 MHz, CDCl$_3$) δ 8.37 (d, 1H, J=2.7 Hz), 8.35 (d, 1H, J=2.7 Hz), 7.37 (dd, 1H, J=8.1, 2.7 Hz), 7.68 (dd, 1H, J=8.1, 2.7 Hz), 7.34 (d, 1H, J=8.1 Hz), 7.32 (d, 1H, J=8.1 Hz), 4.01 (m, 2H), 3.68 (m, 2H), 2.77 (s, 3H), 2.71 (s, 3H), 2.64-1.76 (m, 12H).

Example IV

Preparation of cis and trans-[3-(6-chloropyridin-3-yl)cyclopentyl]-(methyl)oxido-λ$^4$-sulfanylidenecyanamide (4)

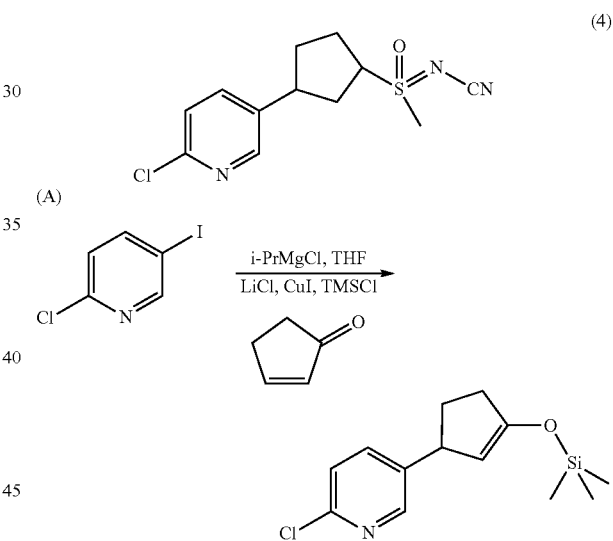

(A)

Lithium chloride (0.11 g, 2.5 mmol) was weighed into an oven-dried, nitrogen-swept 50 mL 3-necked flask and the flask placed under vacuum and heated with a heat gun, cooled and back filled with nitrogen. Copper(I) iodide (0.24 g, 1.3 mmol) and THF (5 mL) were added and the mixture stirred to give homogenous yellow solution. 2-Chloro-5-iodopyridine (3.1 g, 13.1 mmol) was dissolved in THF (25 mL) in an oven dried, nitrogen-swept 100 mL 3-necked flask and the solution cooled to −40° C. under nitrogen and treated with i-PrMgCl (1.4 g, 13.7 mmol, 6.9 mL of a 2 M solution in THF) keeping the internal temperature below −35° C. The flask containing the solubilized copper iodide was treated with trimethylsilyl chloride (1.4 g, 12.4 mmol) and cyclopentenone (1.0 g, 12.4 mmol, filtered through alumina) and cooled to −40° C. and added drop wise, via cannula, to the slurry of the Grignard reagent keeping the internal temperature below −35° C. The mixture was allowed to warm to room temperature over 2 h then diluted with saturated (sat.) NH$_4$Cl/EtOAc and the layers separated, the organic layer dried (Na$_2$SO$_4$), filtered, concentrated and purified by flash silica gel chromatography (hexanes:EtOAc/25:1→2:1) to give 2-chloro-5-(3-trimethylsilanyloxycyclopent-2-enyl)pyridine (0.58 g, 18%) as an oil. $^1$H NMR (300 MHz, CDCl$_3$) δ 8.22 (d, 1H, J=2.4 Hz), 7.48 (dd, 1H, J=8.1, 2.4 Hz), 7.23 (d, 1H, J=8.1 Hz), 4.66 (m, 1H), 3.87 (m, 1H), 2.39 (m, 3H), 1.63 (m, 1H), 0.25 (s, 9H). The bulk of the material isolated from this reaction was 2-chloropyridine.

(B)

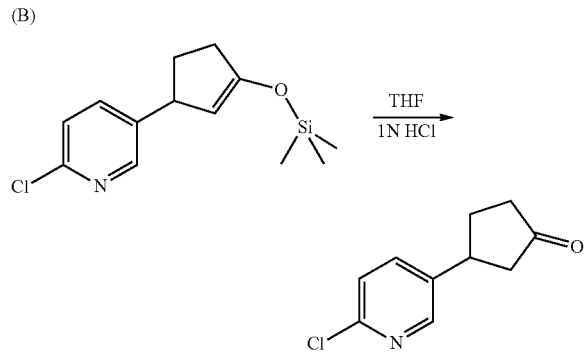

2-Chloro-5-(3-trimethylsilanyloxycyclopent-2-enyl)pyridine (0.58 g, 2.2 mmol) was dissolved in THF (10 mL) in a 100 mL round bottom flask and treated with 1N HCl (2 mL) with stirring at room temperature. After 1 h, the mixture was diluted with EtOAc and sat. NaHCO$_3$ and the layers separated. The aqueous phase was extracted with EtOAc and the combined organic layers dried (Na$_2$SO$_4$), filtered, concentrated, and purified by flash silica gel chromatography (hexanes: EtOAc/2:1) to give 3-(6-chloropyridin-3-yl)cyclopentanone (0.16 g, 37%) as a dark oil: LC/MS (ESI) m/z 195, $^1$H NMR (300 MHz, CDCl$_3$) δ 8.31 (d, 1H, J=2.7 Hz), 7.54 (dd, 1H, J=8.4, 2.7 Hz), 7.31 (d, 1H, J=8.4 Hz), 3.43 (m, 1H), 2.70 (m, 1H), 2.56-2.22 (m, 4H), 1.97 (m, 1H).

(C)

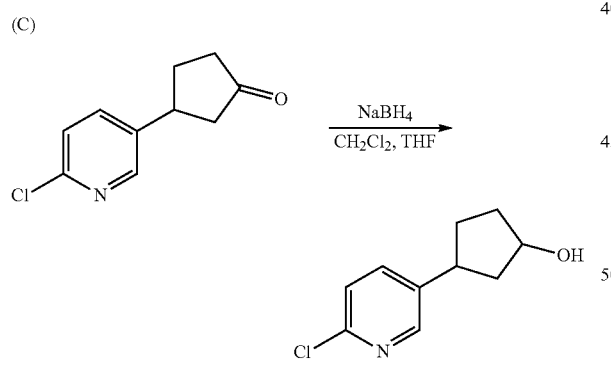

3-(6-Chloropyridin-3-yl)cyclopentanone (0.27 g, 1.4 mmol) was dissolved in CH$_2$Cl$_2$ (10 mL) and MeOH (1 mL) in a 100 mL round bottomed flask and treated with NaBH$_4$ (0.05 g, 1.4 mmol) with stirring at room temperature. After 15 min. the reaction was diluted with water, the layers separated, the aqueous phase extracted with CH$_2$Cl$_2$, and the combined organic layers dried (Na$_2$SO$_4$), filtered and concentrated to give 3-(6-chloropyridin-3-yl)cyclopentanol (0.28 g, 100%) as an oily mixture of cis and trans isomers: LC/MS (ESI) m/z 197, $^1$H NMR (300 MHz, CDCl$_3$) δ 8.27 (m, 2H), 7.65-7.48 (m, 2H), 7.26 (m, 2H), 4.52 (m, 2H), 3.49-2.99 (m, 2H), 2.51-2.01 (m, 4H), 1.99-1.40 m, 10H).

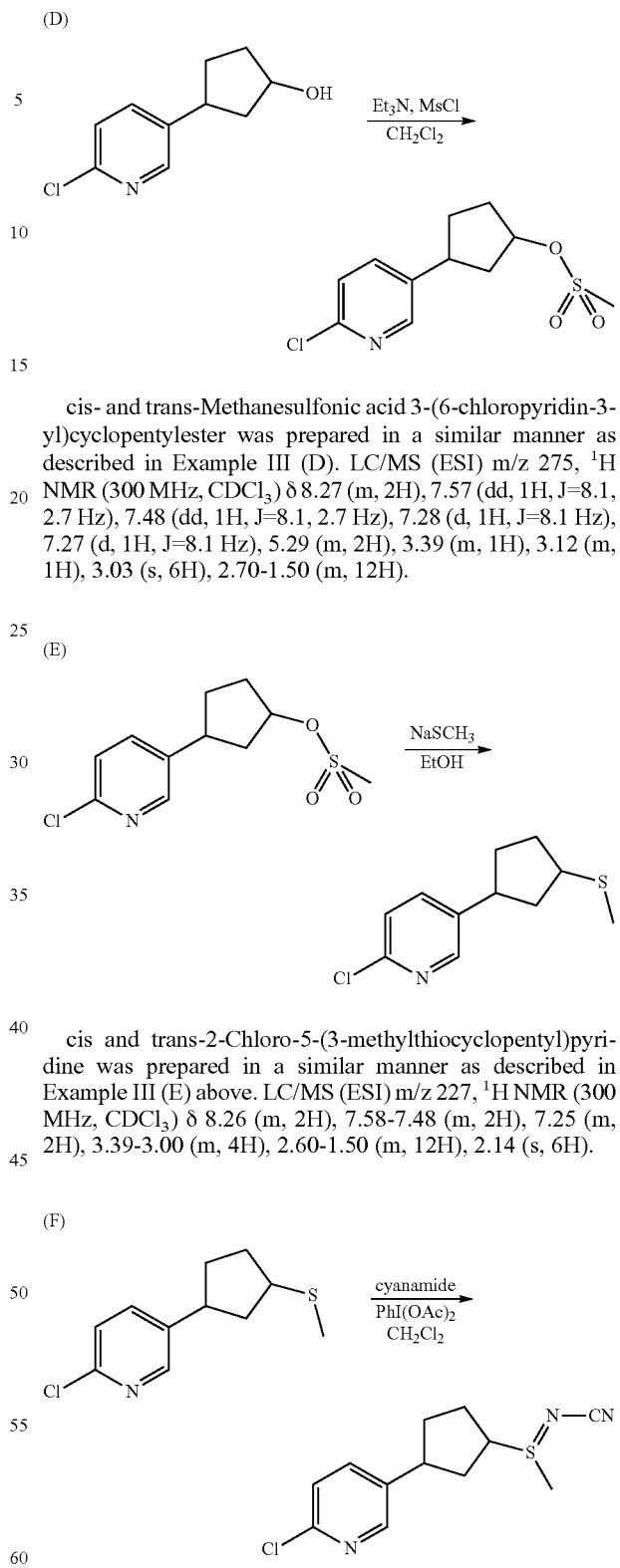

cis- and trans-Methanesulfonic acid 3-(6-chloropyridin-3-yl)cyclopentylester was prepared in a similar manner as described in Example III (D). LC/MS (ESI) m/z 275, $^1$H NMR (300 MHz, CDCl$_3$) δ 8.27 (m, 2H), 7.57 (dd, 1H, J=8.1, 2.7 Hz), 7.48 (dd, 1H, J=8.1, 2.7 Hz), 7.28 (d, 1H, J=8.1 Hz), 7.27 (d, 1H, J=8.1 Hz), 5.29 (m, 2H), 3.39 (m, 1H), 3.12 (m, 1H), 3.03 (s, 6H), 2.70-1.50 (m, 12H).

cis and trans-2-Chloro-5-(3-methylthiocyclopentyl)pyridine was prepared in a similar manner as described in Example III (E) above. LC/MS (ESI) m/z 227, $^1$H NMR (300 MHz, CDCl$_3$) δ 8.26 (m, 2H), 7.58-7.48 (m, 2H), 7.25 (m, 2H), 3.39-3.00 (m, 4H), 2.60-1.50 (m, 12H), 2.14 (s, 6H).

cis and trans-[3-(6-Chloropyridin-3-yl)cyclopentyl](methyl)-λ$^4$-sulfanylidenecyanamide was prepared in a similar manner as described in Example III (F) above, LC/MS (ESI) m/z 267, $^1$H NMR (300 MHz, CDCl$_3$) δ 8.27 (m, 2H), 7.63-7.49 (m, 2H), 7.30 (m, 2H), 3.67 (m, 2H), 3.23 (m, 2H), 2.79 (s, 3H), 2.78 (s, 3H), 2.70-1.70 (m, 12H).

(G)

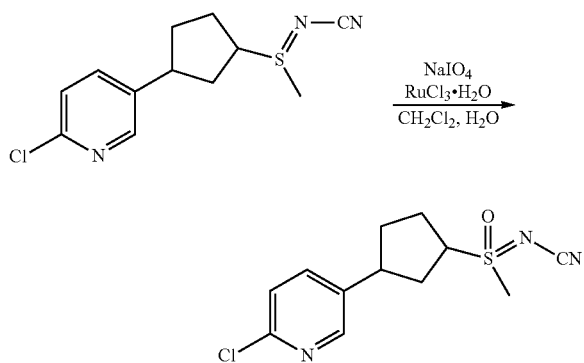

cis and trans-[3-(6-Chloropyridin-3-yl)cyclopentyl](methyl)oxido-λ⁴-sulfanylidenecyanamide was prepared in a similar manner as described in Example III (G) above. LC/MS (ESI) m/z 283, ¹H NMR (300 MHz, CDCl₃) δ 8.26 (m, 2H), 7.68-7.45 (m, 2H), 7.31-7.25 (m, 2H), 3.93 (m, 2H), 3.7-3.15 (m, 2H), 3.25 (s, 3H), 3.24 (s, 3H), 2.82-1.65 (m, 12H).

Example V

Preparation of 1-oxido-3-[6-(trifluoromethyl)pyridin-3-yl]tetrahydro-1H-1λ⁴-thien-1-ylidenecyanamide (5)

(5)

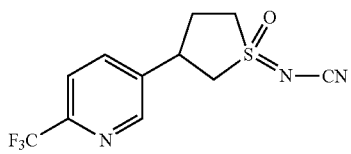

(A)

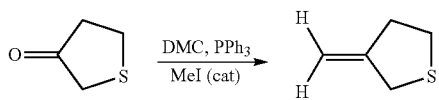

Tetrahydrothiophen-3-one (9.947 g, 97.37 mmol) was placed in a 250 mL Parr bomb. Triphenylphosphine (28.09 g, 108.0 mmol) was added followed by CH₃I (0.30 mL, 4.8 mmol) and dimethyl carbonate (10.0 mL, 119 mmol). The reactor was purged with nitrogen and then heated for 3 h at 175° C. The reaction mixture was cooled to room temperature and purified by Kugelrohr distillation to give 3-methylene tetrahydrothiophene as a colorless liquid (7.65 g) which contained the desired olefin along with methanol and benzene. The desired olefin was used without further purification. ¹H NMR (CDCl₃) δ 4.77 (m, 1H, olefinic H), 4.72 (m, 1H, olefinic H), 2.63 (t, J=7 Hz, 2H, H5), 2.55 (s, 2H, H2), 2.41 (br t, J=7 Hz, 2H, H4). ¹³C{¹H} NMR (CDCl₃) δ 107.3 (olefinic CH₂), 36.7, 35.2, 30.4. GC-MS (ED: 100 [M]⁺.

(B)

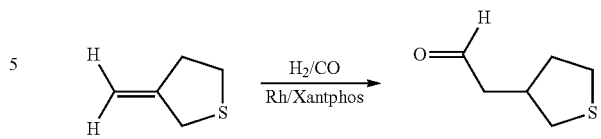

3-Methylene tetrahydrothiophene (5.88 g, as mixture with benzene and methanol) was placed in a 25 mL Parr bomb which contained a magnetic stir bar. Rh(CO)₂(acac) (149 mg, 0.58 mmol) and 4,5-bis(diphenylphosphino)-9,9-dimethylxanthene (Xantphos) (355 mg, 0.61 mmol) were added as solids. The reactor was sealed and purged with CO before pressurized to 350 psi. Hydrogen was then added to bring the total pressure to 700 psi. The reactor was heated to 80° C. with magnetic stirring for 14 h. The reaction mixture was cooled to room temperature. GC-MS indicated the presence of a single aldehyde regioisomer along with benzene and methanol. No starting olefin was evident. Solvent was removed under vacuum, and the product (tetrahydrothiophen-3-yl acetaldehyde) was isolated by Kugelrohr distillation (50° C./0.01 mm) as a colorless liquid (1.1 g). ¹H NMR (acetone-d₆) δ 9.76 (t, J=1.4 Hz, 1H, CH₂CHO), 2.97 (m, 1H), 2.83 (d, J=5.7 Hz, 1H), 2.80 (d, J=5.4 Hz, 1H), 2.62 (br s, 3H), 2.46 (m, 1H), 2.17 (m, 1H), 1.61 (m, 1H). GC-MS (ED: 130 [m]⁺.

(C)

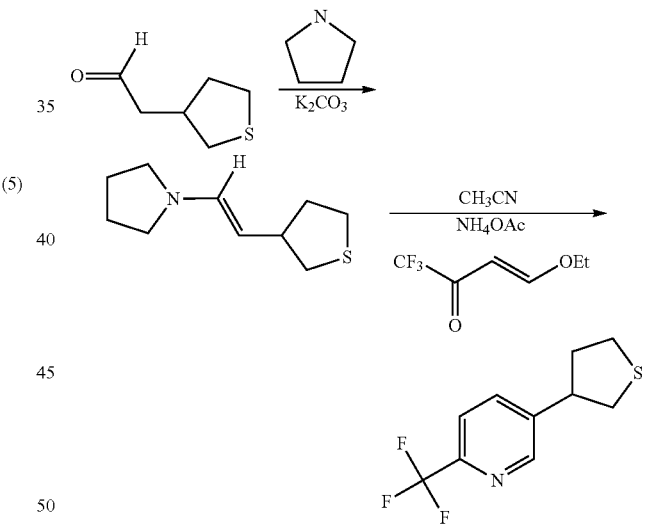

Neat tetrahydrothiophen-3-yl acetaldehyde (1.10 g, 8.45 mmol) was placed in a vial which was purged with nitrogen. The vial was cooled in an ice bath, and solid K₂CO₃ (0.584 g, 4.23 mmol) was added. Neat pyrrolidine (1.70 mL) was added dropwise over 5 min. The ice bath was removed, and the reaction mixture was stirred under N₂ for 20 h. GC-MS showed clean formation of the desired enamine. The solid was washed with four 10 mL portions of ether. The combined ether extracts were evaporated under vacuum to give the intermediate enamine as a light yellow oil (1.617 g). 3-Ethoxy-2-trifluoromethylpropenal (1.634 g, 9.72 mmol) was dissolved in anhydrous CH₃CN (5 mL) under nitrogen. The solution was cooled in an ice bath. A solution of enamine (1.617 g) in 2 mL CH₃CN was added dropwise over 10 min. The ice bath removed and solution allowed to warm to room temperature over 2 h. Ammonium acetate (1.407 g, 18.25 mmol) was added and the reaction mixture was refluxed under nitrogen for 1 h. The solution was cooled to room temperature, and CH₃CN was evaporated under vacuum. The resulting red oil was purified by column chromatography on silica with hexane-ethyl acetate to yield 5-(tetrahydrothiophen-3-yl)-2-(trifluoromethyl)pyridine (1.08 g; 52.3% yield) as an orange crystalline solid. $^1$H NMR (CDCl₃) δ 8.68 (d, J=1.6 Hz, 1H, pyridine H6), 7.83 (dd, J=1.6, 8.0 Hz, 1H, pyridine H4), 7.65 (d, J=8.0 Hz, 1H, pyridine H3), 3.48 (m, 1H), 3.24 (dd, J=6.8, 10 Hz, 1H), 3.09-2.90 (m, 3H), 2.47 (m, 1H), 2.11 (m, 1H). GC-MS (EI): 233 [m]⁺.

(D)

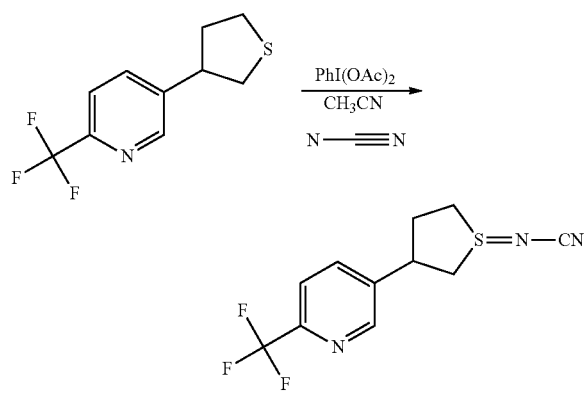

5-(Tetrahydrothiophen-3-yl)-2-trifluoromethylpyridine (1.082 g, 4.64 mmol) was dissolved in 9 mL anhydrous CH₃CN under nitrogen. The solution was cooled in an ice bath. Solid cyanamide (0.195 g, 4.64 mmol) was added followed by iodobenzene diacetate (1.496 g, 4.64 mmol). The reaction mixture was allowed to slowly warm to room temperature overnight. The solution was extracted with hexane (6×30 mL). The acetonitrile layer was concentrated by rotary evaporation, and the residue was triturated with ether. The resulting solid was collected and washed with ether to yield (1E)-3-[6-(trifluoromethyl)pyridin-3-yl]tetrahydro-1H-1λ⁴-thien-1-ylidenecyanamide (1.12 g; 88.4% yield) as an off-white powder. The $^1$H NMR spectrum of this solid exhibited resonances for a 1:1 mixture of diastereomers. $^1$H NMR (acetone-d₆) δ 8.85 (d, J=2.2 Hz, 1H, pyridine H6), 8.83 (d, J=2.2 Hz, 1H, pyridine H6), 8.26 (dd, J=2.2, 8.3 Hz, 1H, pyridine H4), 8.15 (dd, J=2.2, 8.3 Hz, 1H, pyridine H4), 7.90 (d, J=8.3 Hz, 1H, pyridine H3), 7.86 (d, J=8.3 Hz, 1H, pyridine H3), 4.38 (dd, J=8.7, 14 Hz, 1H), 4.23 (tt, J=6, 12 Hz, 1H), 4.16 (ddd, J=2.6, 8.3, 11.2 Hz, 1H), 3.83 (td, J=8.7, 18 Hz, 1H), 3.68-3.48 (m, 3H), 3.29-3.17 (m, 2H), 2.95 (m, 1H), 2.85-2.79 (m, 3H), 2.33 (m, 1H). LC-MS (ELSD): 273 [m]⁺.

(E)

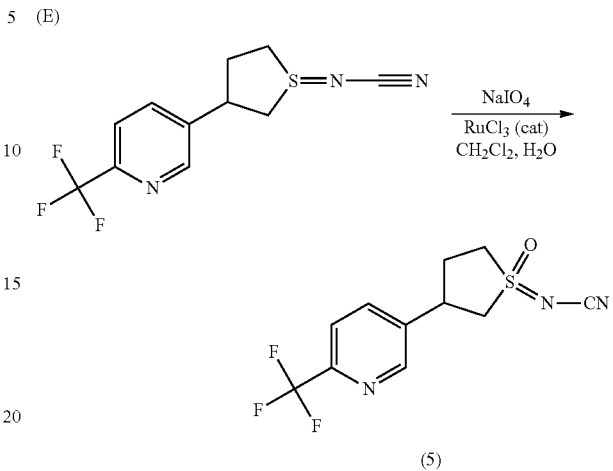

(5)

NaIO₄ (0.870 g, 4.07 mmol) was dissolved in 14 mL water. CH₂Cl₂ (25 mL) was added followed by RuCl₃—H₂O (8 mg, 0.04 mmol, 1 mol %). (1E)-3-[6-(trifluoromethyl)pyridin-3-yl]tetrahydro-1H-1λ⁴-thien-1-ylidenecyanamide (1.00 g, 3.66 mmol) was added in small batches. After 18 h at room temperature, isopropanol (0.5 mL) was added. The two-phase reaction mixture was filtered through a pad of Celite. The organic layer was separated, and the aqueous layer was extracted with CH₂Cl₂. The combined organic extracts were washed with brine, dried (MgSO₄) and concentrated by rotary evaporation to give 1-oxido-3-[6-(trifluoromethyl)pyridin-3-yl]tetrahydro-1H-1λ⁴-thien-1-ylidenecyanamide (5) as an off-white solid which was washed with ether and dried in air (0.36 g, 34% yield). A 1:1 mixture of diastereomers was observed by $^1$H NMR and HPLC. $^1$H NMR (acetone-d₆) δ 8.90 (d, J=2.2 Hz, 1H, pyridine H6), 8.86 (d, J=2.2 Hz, 1H, pyridine H6), 8.26 (dd, J=2.2, 8.3 Hz, 1H, pyridine H4), 8.22 (dd, J=2.2, 8.3 Hz, 1H, pyridine H4), 7.89 (d, J=8.3 Hz, 2H, pyridine H3, both diastereomers), 4.43-3.97 (m, 5H), 3.84-3.64 (m, 5H), 2.93 (m, 2H), 2.83-2.67 (m, 1H), 2.56 (m, 1H). LC-MS (ELSD): 289 [m]⁺.

Table 1 summarizes compounds prepared from either [(6-chloropyridin-3-yl)methyl](methyl)oxido-λ⁴-sulfanylidenecyanamide or [(6-trifluoromethylpyridin-3-yl)methyl](methyl)oxido-λ⁴-sulfanylidenecyanamide according to the alkyation procedures described in either of the examples 1E or 2D above.

TABLE 1

| Cmpd # | Structure | Characterization |
|---|---|---|
| 6 | 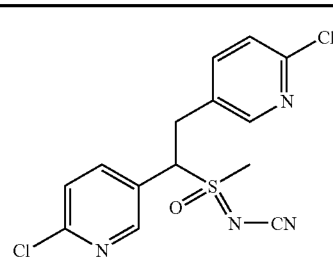 | 1:1 mixture of two diastereomers $^1$H NMR (400 MHz, CDCl₃) δ 8.30 (s, 2H), 8.12 (d, 1H), 8.06 (d, 1H), 7.96 (d, 1H), 7.85 (d, 1H), 7.49 (dd, 2H), 7.37 (ddd, 2H), 7.25 (m, 2H), 4.62 (m, 2H), 4.01 (dd, 1H), 3.92 (dd, 1H), 3.42 (m, 2H), 3.09 (s, 3H), 3.05 (s, 3H); LC-MS (ELSD): Exact mass calcd for C14H12Cl2N4OS [M]+, 355. Found 355. |

TABLE 1-continued

| Cmpd # | Structure | Characterization |
|---|---|---|
| 7 | *(structure: 6-chloropyridin-3-yl with CH(S(O)(Me)=N-CN)CH2-(4-chlorophenyl))* | 1:1 mixture of two diastereomers $^1$H NMR (400 MHz, CDCl$_3$) δ 8.26 (s, 2H), 7.91 (dd, 1H), 7.83 (dd, 1H), 7.45 (dd, 2H), 7.22 (dd, 4H), 6.97 (dd, 4H), 4.56 (dd, 1H), 4.53 (dd, 1H), 3.98 (dd, 1H), 3.89 (dd, 1H), 3.43 (dd, 1H), 3.33 (dd, 1H), 3.04 (s, 3H), 3.00 (s, 3H); LC-MS (ELSD): Exact mass calcd for C15H13Cl2N3OS [M]+, 354. Found 354. |
| 8 | *(structure: 6-chloropyridin-3-yl with CH(S(O)(Me)=N-CN)CH2-(4-methoxyphenyl))* | 1:1 mixture of two diastereomers $^1$H NMR (400 MHz, CDCl$_3$) δ 8.27 (s, 2H), 7.91 (dd, 1H), 7.84 (dd, 1H), 7.44 (dd, 2H), 6.95 (m, 4H), 6.75 (m, 4H), 4.59 (dd, 1H), 4.56 (dd, 1H), 3.92 (dd, 1H), 3.82 (dd, 1H), 3.74 (s, 6H), 3.39 (dd, 1H), 3.30 (dd, 1H), 3.03 (s, 3H), 2.99 (s, 3H); LC-MS (ELSD): Exact mass calcd for C16H17ClN3O2S [M + H]+, 350. Found 350. |
| 9 | *(structure: 6-chloropyridin-3-yl with CH(S(O)(Me)=N-CN)-iPr)* | 1:1 mixture of two diastereomers $^1$H NMR (300 MHz, CDCl$_3$) δ 8.38 (s, 1H), 7.93 (d, 1H), 7.48 (d, 1H), 4.22 and 4.11 (d, 1H), 3.11 and 2.90 (m, 1H), 2.99 (m, 3H), 1.35, 1.10, and 0.93 (m, 6H) LCMS: Mass calcd for C$_{11}$H$_{14}$ClN$_3$OS = 271; Found 272.00 [M + H] & 270.00 [M − H]. |
| 10 | *(structure: 6-chloropyridin-3-yl with CH(S(O)(Me)=N-CN)CH2CH2-OMe)* | 1:1 mixture of two diastereomers $^1$H NMR (400 MHz, CDCl$_3$) δ 8.41 (m, 2H), 7.89 (dd, 1H), 7.85 (dd, 1H), 7.48 (d, 2H), 4.66-4.72 (m, 2H), 3.52-3.58 (m, 2H), 3.242 (s, 3H), 3.327 (s, 3H), 3.08 (s, 3H), 3.05 (s, 3H), 3.00-3.07 (m, 2H), 2.78-2.94 (m, 2H), 2.22-2.39 (m, 2H); LC-MS (ELSD): Exact mass calcd for C11H15ClN3O2S [M + H]+, 288. Found 288. |
| 11 | *(structure: 6-chloropyridin-3-yl with C(S(O)(Me)=N-CN)(CH2OMe)2)* | $^1$H NMR (400 MHz, CDCl$_3$) δ 8.73 (d, 1H), 8.03 (dd, 1H), 7.42 (d, 1H), 4.30 (d, 1H), 4.26 (d, 1H), 4.17 (d, 1H), 4.10 (d, 1H), 3.48 (s, 3H), 3.46 (s, 3H), 3.04 (s, 3H); LC-MS (ELSD): Exact mass calcd for C$_{12}$H$_{17}$ClN$_3$O$_3$S [M + H]$^+$, 318. Found 318. |
| 12 | *(structure: 6-chloropyridin-3-yl with CH(S(O)(Me)=N-CN)CH2CH2F)* | 1:1 mixture of diastereomers. 1H NMR (400 MHz, CDCl3) δ 8.46 (m, 2H), 7.91 (dd, 1H), 7.85 (dd, 1H), 7.51 (dd, 2H), 4.75 (m, 1H), 4.60-4.67 (m, 3H), 4.28 (, 1H), 4.16 (m, 1H), 3.09 (s, 3H), 3.07 (s, 3H), 2.24-2.30 (m, 2H), 1.95-2.00 (m, 2H); LC-MS (ELSD): Mass calc'd for C10H12ClFN3OS [M + H]+, 276. Found 276. |
| 13 | *(structure: 6-chloropyridin-3-yl with CH(S(O)(Me)=N-CN)CH2-cyclopropyl)* | 1:1 mixture of two diastereomers $^1$H NMR (300 MHz, CDCl$_3$) δ 8.48 & 8.47 (m, 1H), 7.92 & 7.91 (m, 1H), 7.51 & 7.49 (m, 1H), 4.52 & 4.50 (m, 1H), 3.05 & 3.02 (s, 3H), 2.45 & 2.10 (m, 2H), 0.50 & 0.18 (m, 5H). LC-MS (ELSD) 284 (M + H), 282 (M − H) |

TABLE 1-continued

| Cmpd # | Structure | Characterization |
|---|---|---|
| 14 | 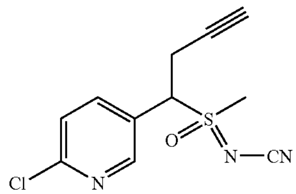 | 1:1 mixture of two diastereomers $^1$H NMR (300 MHz, CDCl$_3$) δ 8.52 & 8.49 (s, 1H), 7.91 & 7.89 (m, 1H), 7.50 & 7.49 (m, 1H), 4.64 & 4.63 (m, 1H), 3.40 & 3.19 (m, 2H), 3.23 & 3.18 (s, 3H), 2.12 (s, 1H). LC-MS (ELSD) 268 (M + H), 266 (M − H) |
| 15 | 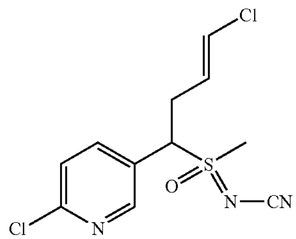 | 1:1 mixture of two diastereomers $^1$H NMR (300 MHz, CDCl$_3$) δ 8.43 & 8.41 (m, 1H), 7.87 & 7.84 (m, 1H), 7.52 & 7.50 (m, 1H), 6.17 & 6.14 (m, 1H), 5.63 & 5.61 (m, 1H), 4.48 & 4.47 (m, 1H), 3.35 & 2.95 (m, 2H), 3.09 & 3.05 (s, 3H). LC-MS (ELSD) 304 (M + H), 302 (M − H) |
| 16 | 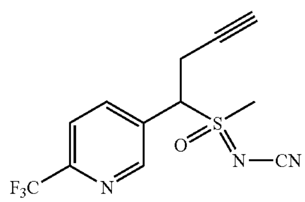 | 1:1 mixture of two diastereomers $^1$H NMR (300 MHz, CDCl$_3$) δ 8.8 & 8.84 (m, 1H), 8.17 & 8.16 (m, 1H), 7.88 & 7.86 (m, 1H), 4.74 & 4.73 (m, 1H), 3.48 & 3.28 (m, 2H), 3.27 & 3.23 (s, 3H), 2.18 & 2.17 (s, 1H). LC-MS (ELSD) 302 (M + H), 300 (M − H) |
| 17 | 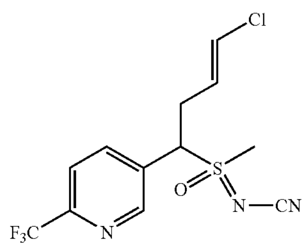 | 1:1 mixture of two diastereomers $^1$H NMR (300 MHz, CDCl$_3$) δ 8.78 & 8.73 (s, 1H), 8.12 & 8.11 (m, 1H), 7.88 & 7.82 (m, 1H), 6.20 & 6.11 (m, 1H), 5.66 & 5.63 (m, 1H), 4.62 & 4.59 (m, 1H), 3.40, 3.07, 3.27 & 2.91 (m, 2H), 3.13 & 3.09 (s, 3H). LC-MS (ELSD) 306 (M + H), 304 (M − H) |
| 18 | 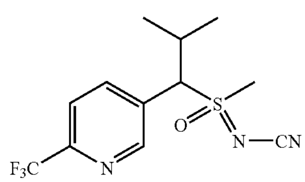 | 1:1 mixture of two diastereomers $^1$H NMR (300 MHz, CDCl$_3$) δ 8.75 & 8.73 (s, 1H), 8.21 & 8.19 (m, 1H), 7.86 & 7.85 (m, 1H), 4.23 & 4.24 (m, 1H), 3.17 & 2.99 (m, 1H), 3.02 (s, 3H), 1.39-1.13, & 1.38-1.15 (m, 6H). LC-MS (ELSD) 338 (M + H), 336 (M − H) |

Example VI

Insecticidal Testing

The compounds identified in the foregoing examples (compounds 1-5) and in Table 1 (compounds 6-18) were tested against cotton aphid and green peach aphid using procedures described hereinafter.

Insecticidal Test for Cotton Aphid (*Aphis gossypii*) in Foliar Spray Assay

Squash with fully expanded cotyledon leaves were trimmed to one cotyledon per plant and infested with cotton aphid (wingless adult and nymph) 1 day prior to chemical application. Each plant was examined before chemical application to ensure proper infestation (ca. 30-70 aphids per plant). Compounds (2 mg) were dissolved in 2 ml of acetone:methanol (1:1) solvent, forming stock solutions of 1000 ppm. The stock solutions were diluted 5× with 0.025% Tween 20 in H$_2$O to obtain the highest test solution at 200 ppm. Lower test concentrations (50, 12.5, 3.13 and 0.78 ppm) were prepared by making sequential 4× dilutions from the 200 ppm solution with a diluent consisting 80 parts of 0.025% Tween 20 in H$_2$O and 20 parts of acetone:methanol (1:1). A hand-held Devilbiss sprayer was used to apply the spray solutions until runoff to both sides of the squash cotyledon leaves. Four plants (4 replications) were used for each concentration of each compound. Reference plants (solvent check) were sprayed with the diluent only. Treated plants were held in a holding room for 3 days at approximately 23° C. and 40% RH before the number of live aphids on each plant was recorded. Insecticidal activity was measured by Corrected % Control using Abbott's correction formula and the values for the lower test concentrations are presented in Table 2:

Corrected % Control=100*(X−Y)/X where X=No. of live aphids on solvent check plants
Y=No. of live aphids on treated plants Insecticidal Test for Green Peach Aphid (*Myzus persicae*) in Foliar Spray Assay Cabbage seedlings grown in 3-inch pots, with 2-3 small (3-5 cm) true leaves, were used as test substrate. The seedlings were infested with 20-50 green peach aphids (wingless adult and nymph) 2-3 days prior to chemical application. Four seedlings were used for each treatment. Compounds (2 mg) were dissolved in 2 ml of acetone:methanol (1:1) solvent, forming stock solutions of 1000 ppm. The stock solutions were diluted 5× with 0.025% Tween 20 in $H_2O$ to obtain the highest test solution at 200 ppm. A lower test concentration of 50 ppm was prepared by making a 4× dilution from the 200 ppm solution with a diluent consisting 80 parts of 0.025% Tween 20 in $H_2O$ and 20 parts of acetone:methanol (1:1). A hand-held Devilbiss sprayer was used for spraying a solution to both sides of cabbage leaves until runoff. Reference plants (solvent check) were sprayed with the diluent only. Treated plants were held in a holding room for three days at approximately 23° C. and 40% RH prior to grading. Evaluation was conducted by counting the number of live aphids per plant under a microscope. Insecticidal activity was measured by using Abbott's correction formula:

Corrected % Control=$100*(X-Y)/X$ where X=No. of live aphids on solvent check plants
Y=No. of live aphids on treated plants
The Corrected % Control values from the above assays are given in Table 2

TABLE 2

| Comp # | CA 200 | CA 50 | GPA 200 | GPA 50 |
|---|---|---|---|---|
| 1 | A | A | G | G |
| 2 | A | A | C | G |
| 3 | D | G | D | G |
| 4 | A | C | B | G |
| 5 | A | A | B | E |
| 6 | A | A | G | G |
| 7 | A | A | G | G |
| 8 | A | A | G | G |
| 9 | A | A | G | G |
| 10 | A | A | D | G |
| 11 | A | A | G | G |
| 12 | A | A | A | A |
| 13 | A | A | H | H |
| 14 | A | A | G | G |
| 15 | A | A | G | G |
| 16 | A | A | A | B |
| 17 | A | A | A | C |
| 18 | A | A | A | D |

CA 200 refers to % control at 200 ppm against cotton aphid in foliar spray tests,
CA 50 refers to % control at 50 ppm against cotton aphid in foliar spray tests,
GPA 200 refers to % control at 200 ppm against green peach aphid in foliar spray tests,
GPA 50 refers to % control at 50 ppm against green peach aphid in foliar spray tests.

In each case of Table 2 the rating scale is as follows:

| % Control (or Mortality) | Rating |
|---|---|
| 90-100 | A |
| 80-89 | B |
| 70-79 | C |
| 60-69 | D |
| 50-59 | E |
| Less than 50 | F |
| Inactive | G |
| Not tested | H |

The compounds that showed good activity against both aphid species in Table 2 were further tested with multiple lower doses (rundown assays) against cotton aphid using procedures described above. Results are shown in Table 3.

TABLE 3

| | % Control at ppm against cotton aphid on squash, foliar spray | | | |
|---|---|---|---|---|
| Comp # | 0.781 ppm | 3.125 ppm | 12.5 ppm | 50 ppm |
| 2 | C | A | A | A |
| 5 | F | C | A | A |
| 12 | A | A | A | A |
| 16 | B | A | A | A |
| 17 | D | B | A | A |
| 18 | A | A | A | A |

In each case of Table 3 the rating scale is the same as that used for Table 2.

Insecticide Utility

The compounds of the invention are useful for the control of invertebrates including insects. Therefore, the present invention also is directed to a method for inhibiting an insect which comprises applying an insect-inhibiting amount of a compound of formula (I) to a locus of the insect, to the area to be protected, or directly on the insect to be controlled. The compounds of the invention may also be used to control other invertebrate pests such as mites and nematodes.

The "locus" of insects or other pests is a term used herein to refer to the environment in which the insects or other pests live or where their eggs are present, including the air surrounding them, the food they eat, or objects which they contact. For example, insects which eat, damage or contact edible, commodity, ornamental, turf or pasture plants can be controlled by applying the active compounds to the seed of the plant before planting, to the seedling, or cutting which is planted, the leaves, stems, fruits, grain, and/or roots, or to the soil or other growth medium before or after the crop is planted. Protection of these plants against virus, fungus or bacterium diseases may also be achieved indirectly through controlling sap-feeding pests such as whitefly, plant hopper, aphid and spider mite. Such plants include those which are bred through conventional approaches and which are genetically modified using modern biotechnology to gain insect-resistant, herbicide-resistant, nutrition-enhancement, and/or any other beneficial traits.

It is contemplated that the compounds might also be useful to protect textiles, paper, stored grain, seeds and other foodstuffs, houses and other buildings which may be occupied by humans and/or companion, farm, ranch, zoo, or other animals, by applying an active compound to or near such objects. Domesticated animals, buildings or human beings might be protected with the compounds by controlling invertebrate and/or nematode pests that are parasitic or are capable of transmitting infectious diseases. Such pests include, for example, chiggers, ticks, lice, mosquitoes, flies, fleas and heartworms. Nonagronomic applications also include invertebrate pest control in forests, in yards, along road sides and railroad right of way.

The term "inhibiting an insect" refers to a decrease in the numbers of living insects, or a decrease in the number of viable insect eggs. The extent of reduction accomplished by a compound depends, of course, upon the application rate of the compound, the particular compound used, and the target insect species. At least an inactivating amount should be used. The term "insect-inactivating amount" is used to describe the amount, which is sufficient to cause a measurable reduction in the treated insect population. Generally an amount in the range from about 1 to about 1000 ppm by weight active compound is used. For example, insects or other pests which can be inhibited include, but are not limited to:

Lepidoptera—*Heliothis* spp., *Helicoverpa* spp., *Spodoptera* spp., *Mythimna unipuncta*, *Agrotis ipsilon*, *Earias* spp., *Euxoa auxiliaris*, *Trichoplusia ni*, *Anticarsia gemmatalis*, *Rachiplusia nu*, *Plutella xylostella*, *Chilo* spp., *Scirpophaga incertulas*, *Sesamia inferens*, *Cnaphalocrocis medinalis*, *Ostrinia nubilalis*, *Cydia pomonella*, *Carposina niponensis*, *Adoxophyes orana*, *Archips argyrospilus*, *Pandemis heparana*, *Epinotia aporema*, *Eupoecilia ambiguella*, *Lobesia botrana*, *Polychrosis viteana*, *Pectinophora gossypiella*, *Pieris rapae*, *Phyllonorycter* spp., *Leucoptera malifoliella*, *Phyllocnisitis citrella*

Coleoptera—*Diabrotica* spp., *Leptinotarsa decemlineata*, *Oulema oryzae*, *Anthonomus grandis*, *Lissorhoptrus oryzophilus*, *Agriotes* spp., *Melanotus communis*, *Popillia japonica*, *Cyclocephala* spp., *Tribolium* spp.

Homoptera—*Aphis* spp., *Myzus persicae*, *Rhopalosiphum* spp., *Dysaphis plantaginea*, *Toxoptera* spp., *Macrosiphum euphorbiae*, *Aulacorthum solani*, *Sitobion avenae*, *Metopolophium dirhodum*, *Schizaphis graminum*, *Brachycolus noxius*, *Nephotettix* spp., *Nilaparvata lugens*, *Sogatella furcifera*, *Laodelphax striatellus*, *Bemisia tabaci*, *Trialeurodes vaporariorum*, *Aleurodes proletella*, *Aleurothrixus floccosus*, *Quadraspidiotus perniciosus*, *Unaspis yanonensis*, *Ceroplastes rubens*, *Aonidiella aurantii*

Hemiptera—*Lygus* spp., *Eurygaster maura*, *Nezara viridula*, *Piezodorus guildingi*, *Leptocorisa varicornis*, *Cimex lectularius*, *Cimex hemipterus*

Thysanoptera—*Frankliniella* spp., *Thrips* spp., *Scirtothrips dorsalis*

Isoptera—*Reticulitermes flavipes*, *Coptotermes formosanus*, *Reticulitermes virginicus*, *Heterotermes aureus*, *Reticulitermes hesperus*, *Coptotermes frenchii*, *Shedorhinotermes* spp., *Reticulitermes santonensis*, *Reticulitermes grassei*, *Reticulitermes banyulensis*, *Reticulitermes speratus*, *Reticulitermes hageni*, *Reticulitermes tibialis*, *Zootermopsis* spp., *Incisitermes* spp., *Marginitermes* spp., *Macrotermes* spp., *Microcerotermes* spp., *Microtermes* spp.

Diptera—*Liriomyza* spp., *Musca domestica*, *Aedes* spp., *Culex* spp., *Anopheles* spp., *Fannia* spp., *Stomoxys* spp., Hymenoptera—*Iridomyrmex humilis*, *Solenopsis* spp., *Monomorium pharaonic*, *Atta* spp., *Pogonomyrmex* spp., *Camponotus* spp., *Monomorium* spp., *Tapinoma sessile*, *Tetramorium* spp., *Xylocapa* spp., *Vespula* spp., *Polistes* spp.

Mallophaga (chewing lice)

Anoplura (sucking lice)—*Pthirus pubis*, *Pediculus* spp.

Orthoptera (grasshoppers, crickets)—*Melanoplus* spp., *Locusta migratoria*, *Schistocerca gregaria*, *Gryllotalpidae* (mole crickets).

Blattoidea (cockroaches)—*Blatta orientalis*, *Blattella germanica*, *Periplaneta americana*, *Supella longipalpa*, *Periplaneta australasiae*, *Periplaneta brunnea*, *Parcoblatta pennsylvanica*, *Periplaneta fuliginosa*, *Pycnoscelus surinamensis*, Siphonaptera—*Ctenophalides* spp., *Pulex irritans*

Acari—*Tetranychus* spp., *Panonychus* spp., *Eotetranychus carpini*, *Phyllocoptruta oleivora*, *Aculus pelekassi*, *Brevipalpus phoenicis*, *Boophilus* spp., *Dermacentor variabilis*, *Rhipicephalus sanguineus*, *Amblyomma americanum*, *Ixodes* spp., *Notoedres cati*, *Sarcoptes scabiei*, *Dermatophagoides* spp.

Nematoda—*Dirofilaria immitis*, *Meloidogyne* spp., *Heterodera* spp., *Hoplolaimus columbus*, *Belonolaimus* spp., *Pratylenchus* spp., *Rotylenchus reniformis*, *Criconemella ornata*, *Ditylenchus* spp., *Aphelenchoides besseyi*, *Hirschmanniella* spp.

Compositions

The compounds of this invention are applied in the form of compositions which are important embodiments of the invention, and which comprise a compound of this invention and a phytologically-acceptable inert carrier. Control of the pests is achieved by applying compounds of the invention in forms of sprays, topical treatment, gels, seed coatings, microcapsulations, systemic uptake, baits, eartags, boluses, foggers, fumigants aerosols, dusts and many others. The compositions are either concentrated solid or liquid formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and/or nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been preformed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations from 10 ppm to 5000 ppm by weight of compound are expected to provide good control. With many of the compounds, concentrations from 100 to 1500 ppm will suffice.

The locus to which a compound is applied can be any locus inhabited by an insect or mite, for example, vegetable crops, fruit and nut trees, grape vines, ornamental plants, domesticated animals, the interior or exterior surfaces of buildings, and the soil around buildings.

Because of the unique ability of insect eggs to resist toxicant action, repeated applications may be desirable to control newly emerged larvae, as is true of other known insecticides and acaricides.

Systemic movement of compounds of the invention in plants may be utilized to control pests on one portion of the plant by applying the compounds to a different portion of it. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal proteins, those expressing herbicide resistance, such as "Roundup Ready®" seed, or those with "stacked" foreign genes expressing insecticidal proteins, herbicide resistance, nutrition-enhancement and/or any other beneficial traits.

An insecticidal bait composition consisting of compounds of the present invention and attractants and/or feeding stimulants may be used to increase efficacy of the insecticides against insect pest in a device such as trap, bait station, and the like. The bait composition is usually a solid, semi-solid (including gel) or liquid bait matrix including the stimulants and one or more non-microencapsulated or microencapsulated insecticides in an amount effective to act as kill agents.

The compounds of the present invention (Formula I) are often applied in conjunction with one or more other insecticides or fungicides or herbicides to obtain control of a wider variety of pests diseases and weeds. When used in conjunction with other insecticides or fungicides or herbicides, the presently claimed compounds can be formulated with the other insecticides or fungicides or herbicide, tank mixed with the other insecticides or fungicides or herbicides, or applied sequentially with the other insecticides or fungicides or herbicides.

Some of the insecticides that can be employed beneficially in combination with the compounds of the present invention include: antibiotic insecticides such as allosamidin and thuringiensin; macrocyclic lactone insecticides such as spinosad, spinetoram, and other spinosyns including the 21-butenyl spinosyns and their derivatives; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; biological insecticides such as *Bacillus popilliae*, *B. sphaericus*, *B. thuringiensis* subsp. *aizawai*, *B. thuringiensis* subsp. *kurstaki*, *B. thuringiensis* subsp. *tenebrionis*, *Beauveria bassiana*, *Cydia pomonella* granulosis virus, Douglas fir tussock moth NPV, gypsy moth NPV, *Helicoverpa zea* NPV, Indian meal moth granulosis virus, *Metarhizium anisopliae*, *Nosema locustae*, *Paecilomyces fumosoroseus*, *P. lilacinus*, *Photorhabdus luminescens*, *Spodoptera exigua* NPV, trypsin modulating oostatic factor, *Xenorhabdus nematophilus*, and *X. bovienii*, plant incorporated protectant insecticides such as Cry1Ab, Cry1Ac, Cry1F, Cry1A.105, Cry2Ab2, Cry3A, mir Cry3A, Cry3Bb1, Cry34, Cry35, and VIP3A; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methyl-chloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-5-methyl, demeton-5-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphosethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophosethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cis-methrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spirodiclofen, spiromesifen and spirotetramat; thiourea insecticides such as diafenthiuron; urea insecticides such as flucofuron and sulcofuron; and unclassified insecticides such as AKD-3088, closantel, crotamiton, cyflumetofen, E2Y45, EXD, fenazaflor, fenazaquin, fenoxacrim, fenpyroximate, FKI-1033, flubendiamide, HGW86, hydramethylnon, IKI-2002, isoprothiolane, malonoben, metaflumizone, metoxadiazone, nifluridide, NNI-9850, NNI-0101, pymetrozine, pyridaben, pyridalyl, Qcide, rafoxanide, rynaxypyr, SYJ-159, triarathene and triazamate and any combinations thereof.

Some of the fungicides that can be employed beneficially in combination with the compounds of the present invention include: 2-(thiocyanatomethylthio)-benzothiazole, 2-phenylphenol, 8-hydroxyquinoline sulfate, Ampelomyces, quisqualis, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, kasugamycin, kasugamycin hydrochloride hydrate, kresoxim-methyl, mancopper, mancozeb, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyributicarb, pyrifenox, pyrimethanil, pyroquilon, quinoclamine, quinoxyfen, quintozene, Reynoutria sachalinensis extract, silthiofam, simeconazole, sodium 2-phenylphenoxide, sodium bicarbonate, sodium pentachlorophenoxide, spiroxamine, sulfur, SYP-Z071, tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, *Candida oleophila, Fusarium oxysporum, Gliocladium* spp., *Phlebiopsis gigantean, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, and any combinations thereof.

Some of the herbicides that can be employed in conjunction with the compounds of the present invention include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flampropand flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, fluorochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac.

We claim:

1. A method of controlling insects which comprises applying to a locus where control is desired an insect-inactivating amount of a compound of the formula (I)

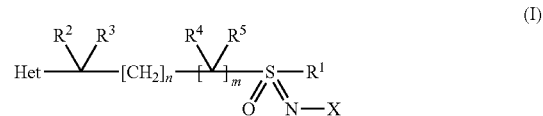

wherein
Het represents

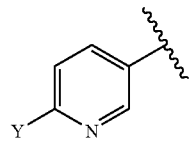

Y represents halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, CN, or $NO_2$;
X represents $NO_2$, CN, or $COOR^7$;
n and m independently represent integers from 0-1;
$R^1$ represents $C_1$-$C_4$ alkyl;
$R^2$ represents H, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkoxy substituted $C_1$-$C_4$ alkyl, halo, CN, COOR$^7$, COR$^8$, CONR$^7$R$^8$, aryl, or arylalkyl;

R$^3$ represents H, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkoxy substituted $C_1$-$C_4$ alkyl, halo, CN, SO$_p$R$^6$, COOR$^7$, CONR$^7$R$^8$, aryl, or arylalkyl;

R$^4$ represents H, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, CN, SO$_p$R$^6$, COOR$^7$, CONR$^7$R$^8$, aryl, or arylalkyl;

R$^5$ represents H, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, CN, SO$_p$R$^6$, COOR$^7$, CONR$^7$R$^8$, aryl, or arylalkyl;

R$^6$ represents $C_1$-$C_4$ alkyl or $C_1$-$C_4$ haloalkyl;

R$^7$ represents $C_1$-$C_4$ alkyl, $C_1$-$C_4$ haloalkyl, $C_3$-$C_6$ alkenyl, $C_3$-$C_6$ alkynyl, $C_3$-$C_6$ haloalkenyl, aryl, or arylalkyl; and R$^8$ represents H, $C_1$-$C_4$ alkyl, $C_1$-$C_4$ haloalkyl, $C_3$-$C_6$ alkenyl, $C_3$-$C_6$ alkynyl, $C_3$-$C_6$ haloalkenyl, aryl, or arylalkyl;

with the proviso that when Het represents 6-halopyridin-3-yl, 6-($C_1$-$C_4$)alkylpyridin-3-yl, or 6-($C_1$-$C_4$)alkoxypyridin-3-yl, 6-($C_1$-$C_4$)haloalkylpyridin-3-yl, then R$^2$, R$^3$, R$^4$ and R$^5$ do not represent hydrogen, methyl, ethyl or halo.

2. A method of claim 1 wherein Y represents halogen, $C_1$-$C_4$ alkyl, $C_1$-$C_4$ haloalkyl, $C_1$-$C_4$ alkoxy, $C_1$-$C_4$ haloalkoxy, CN, or NO$_2$.

3. A method of claim 1 in which Y is halo or $C_1$-$C_4$ haloalkyl.

4. A method of claim 1 in which X is NO$_2$ or CN.

5. A method of claim 1 in which m and n represent 0.

6. A method of claim 1 in which R$^1$ represents CH$_3$ or CH$_2$CH$_3$.

7. A method of claim 1 in which R$^2$ represents $C_1$-$C_4$ alkyl, $C_1$-$C_4$ haloalkyl, $C_2$-$C_4$ haloalkenyl, $C_2$-$C_4$ alkynyl, $C_1$-$C_4$ alkoxy substituted $C_1$-$C_4$ alkyl, or arylalkyl and R$^3$ represents hydrogen.

8. A method of claim 1 wherein said compound is part of a composition which comprises a said compound in combination with a phytologically-acceptable carrier.

* * * * *